(12) United States Patent
Okada

(10) Patent No.: US 8,192,431 B2
(45) Date of Patent: Jun. 5, 2012

(54) ENDOSCOPIC TREATMENT INSTRUMENT

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 1047 days.

(21) Appl. No.: 10/785,827

(22) Filed: Feb. 24, 2004

(65) Prior Publication Data

US 2004/0172018 A1 Sep. 2, 2004

(30) Foreign Application Priority Data

Feb. 28, 2003 (JP) .................................. 2003-054644

(51) Int. Cl.
*A61B 18/04* (2006.01)

(52) U.S. Cl. ............... 606/46; 606/41; 606/42; 606/43; 606/44; 606/45; 606/47; 606/48; 606/49

(58) Field of Classification Search .......... 606/1, 27–52, 606/110, 167, 205; 600/101, 104, 106, 129, 600/153

See application file for complete search history.

(56) References Cited

U.S. PATENT DOCUMENTS

| | | | | |
|---|---|---|---|---|
| 3,915,157 A | * | 10/1975 | Mitsui | 600/107 |
| 4,436,087 A | * | 3/1984 | Ouchi | 600/106 |
| 4,747,406 A | * | 5/1988 | Nash | 606/159 |
| 4,790,813 A | * | 12/1988 | Kensey | 604/22 |
| 4,802,487 A | * | 2/1989 | Martin et al. | 600/463 |
| 4,840,176 A | * | 6/1989 | Ohno | 606/47 |
| 5,037,433 A | * | 8/1991 | Wilk et al. | 606/139 |
| 5,766,184 A | * | 6/1998 | Matsuno et al. | 606/142 |
| 5,849,011 A | * | 12/1998 | Jones et al. | 606/47 |
| 6,352,503 B1 | * | 3/2002 | Matsui et al. | 600/104 |
| 6,602,262 B2 | * | 8/2003 | Griego et al. | 606/113 |
| 6,699,180 B2 | * | 3/2004 | Kobayashi | 600/127 |
| 2002/0161333 A1 | * | 10/2002 | Luther | 604/167.01 |

FOREIGN PATENT DOCUMENTS

| | | |
|---|---|---|
| JP | 60-184513 | 12/1985 |
| JP | 62-50610 | 3/1987 |
| JP | 5-293118 | 11/1993 |
| JP | 8-126648 | 5/1996 |
| JP | 8-299355 | 11/1996 |

OTHER PUBLICATIONS

Oyama, T., et al., "Endoscopic Mucosal Resection Using a Hooking Knife (Hooking EMR)", Stomach and Intestine, Aug. 2002, vol. 37, No. 9, pp. 11155-1161.

* cited by examiner

*Primary Examiner* — Aaron Roane
(74) *Attorney, Agent, or Firm* — Scully, Scott, Murphy & Presser, P.C.

(57) ABSTRACT

An engaging mechanism, which restricts rotation of a cutter section about an axis of a sheath, is provided. In accordance with an advancing/retreating operation of an operation wire by an operation slider, switching is made between a rotation restriction position where rotational restriction of the cutter section is effected by the engaging mechanism and a restriction release position where the cutter section is released from the rotation restriction position and is made rotatable about the axis of the sheath relative to the sheath.

7 Claims, 20 Drawing Sheets

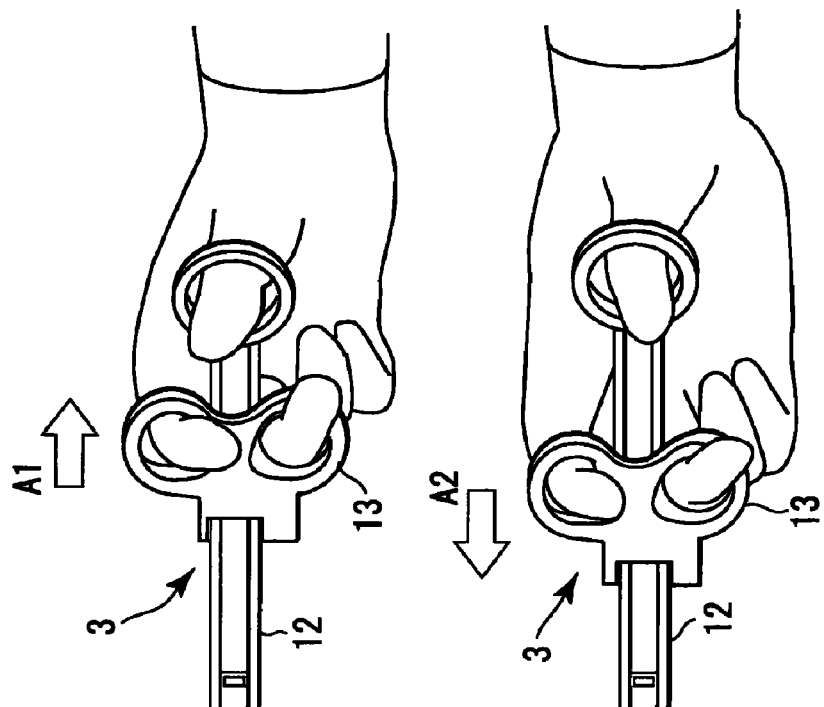
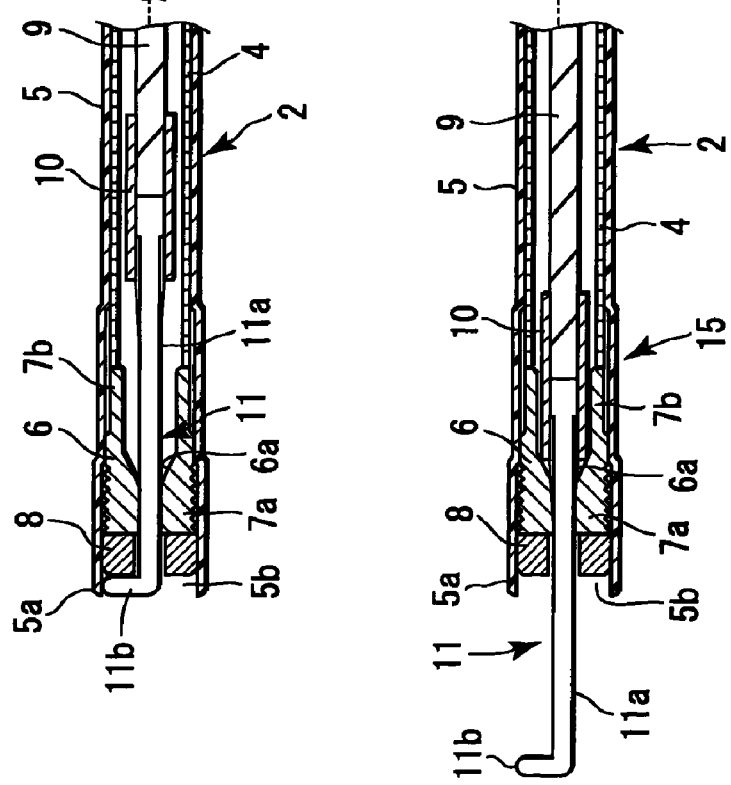

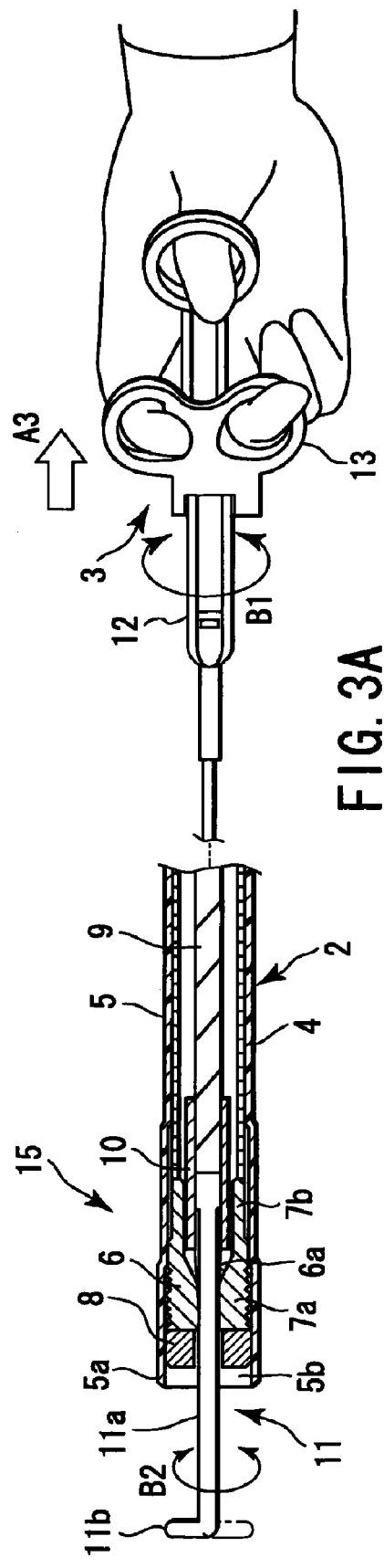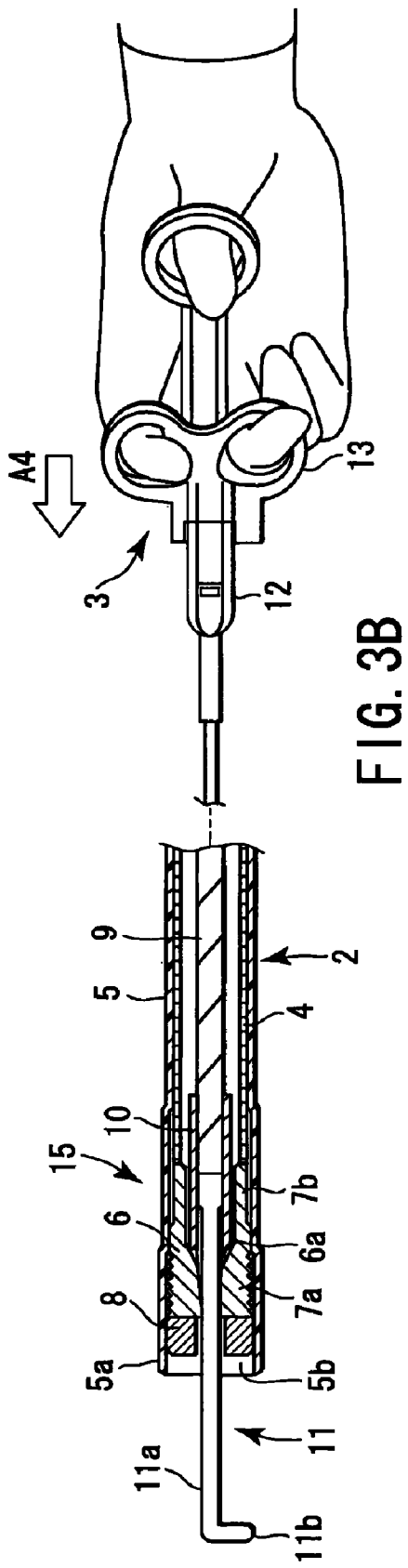
FIG. 3A
FIG. 3B

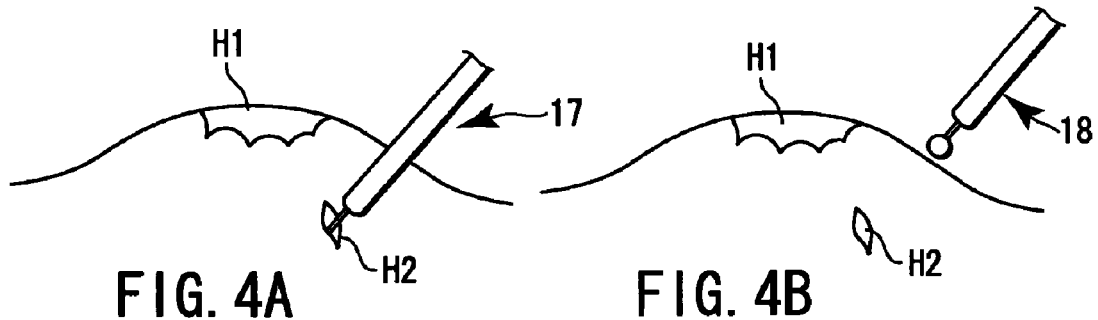
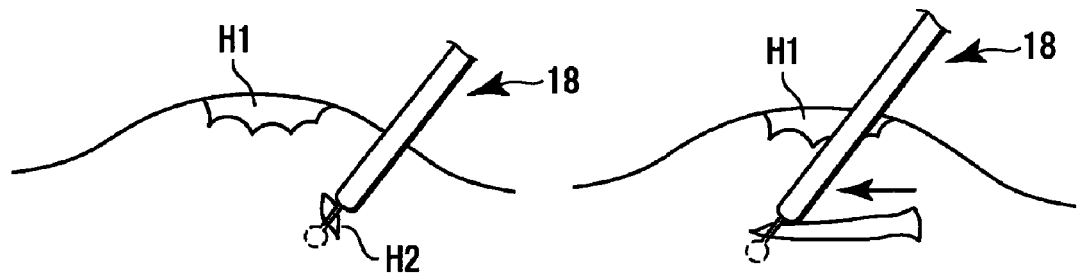
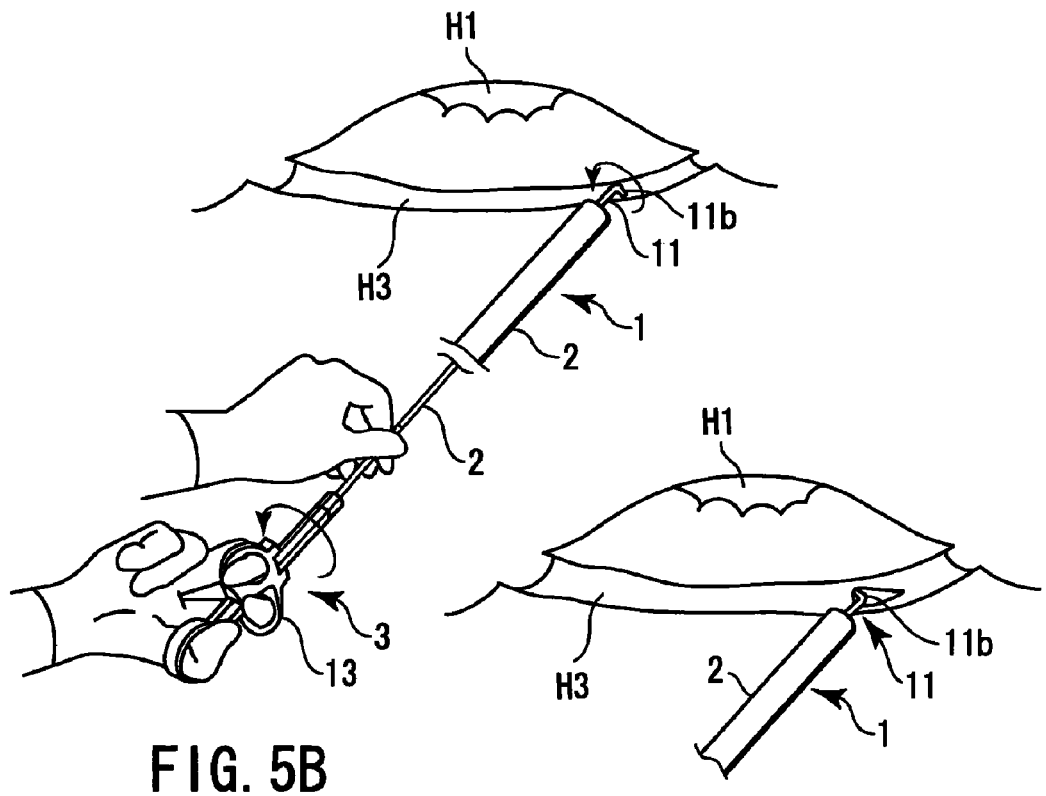

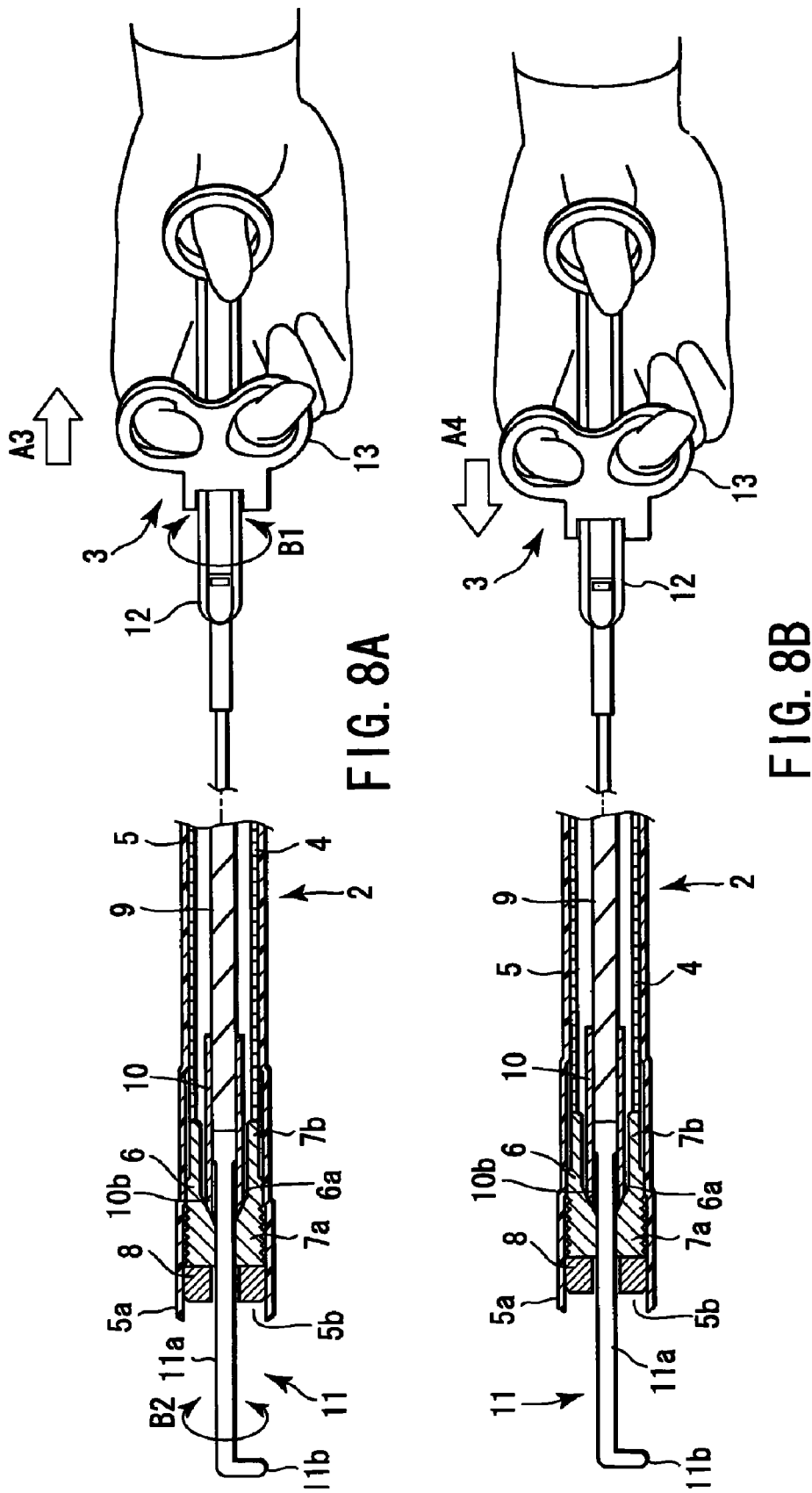

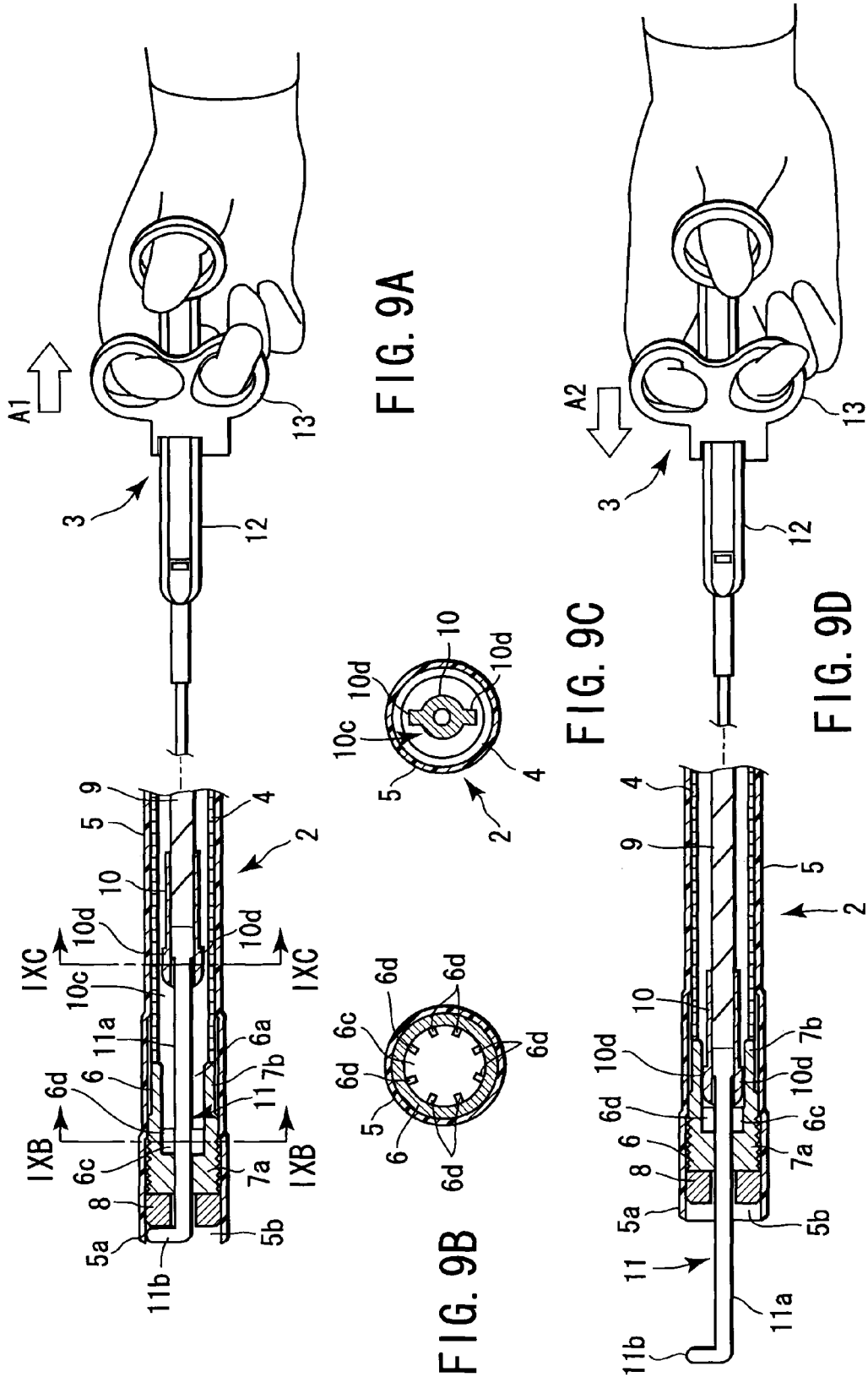

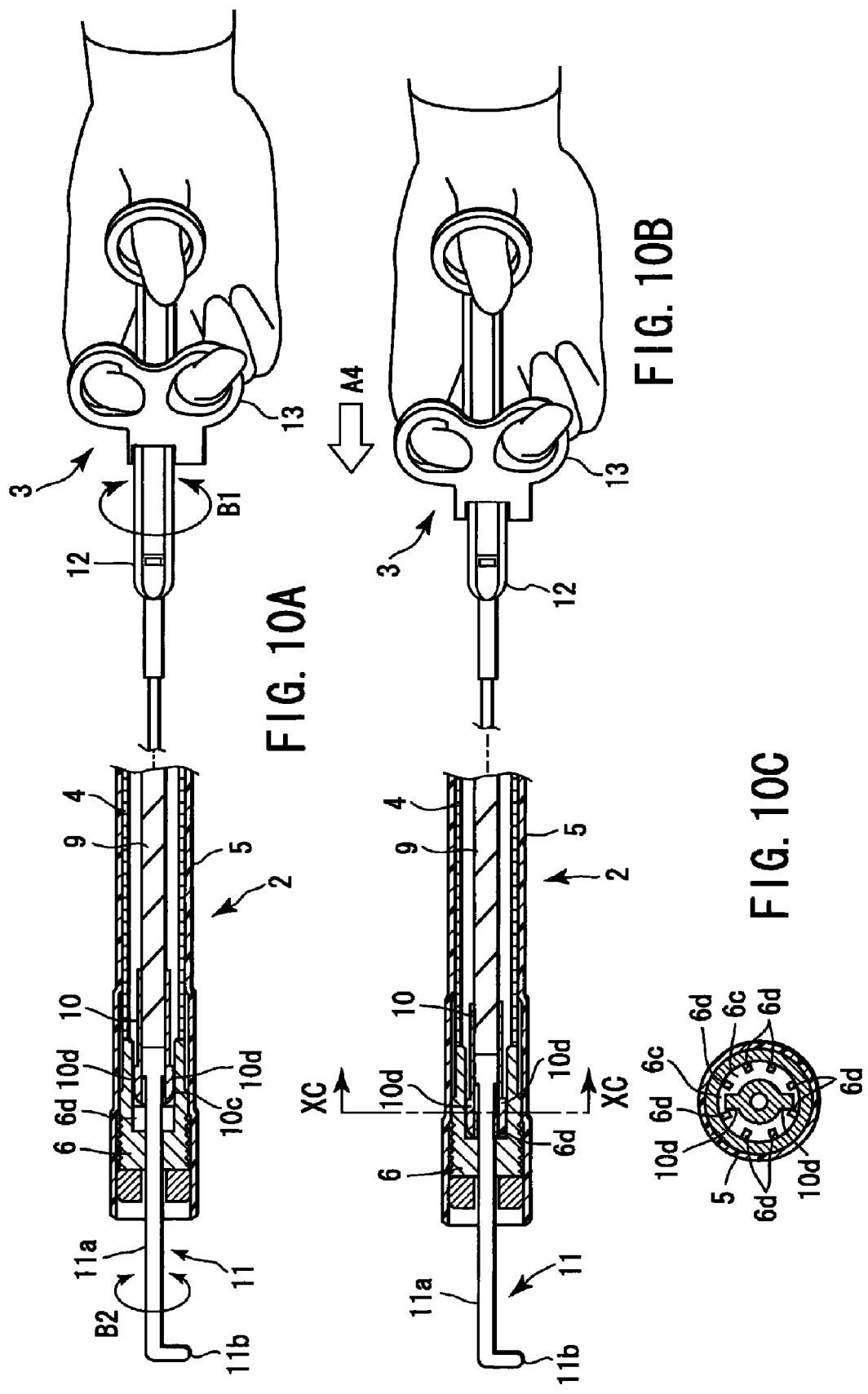

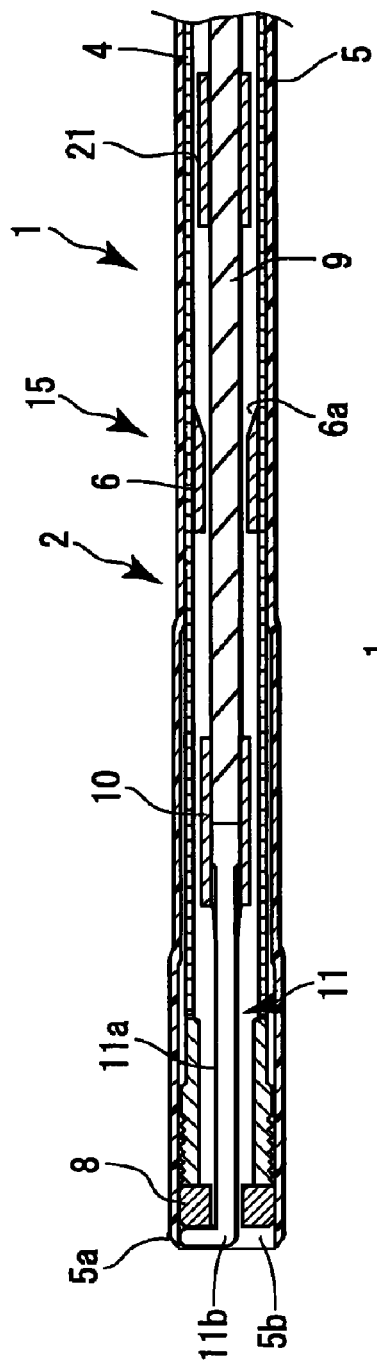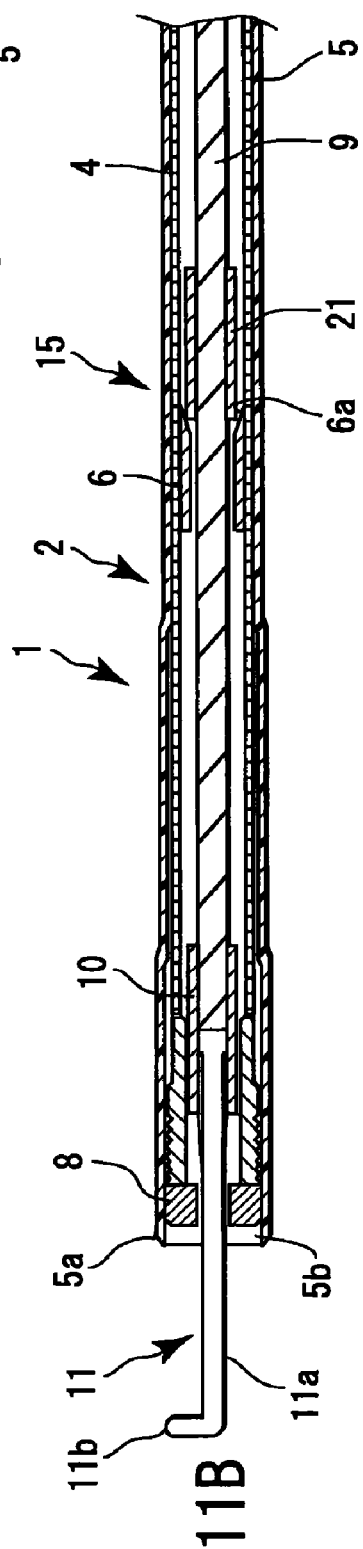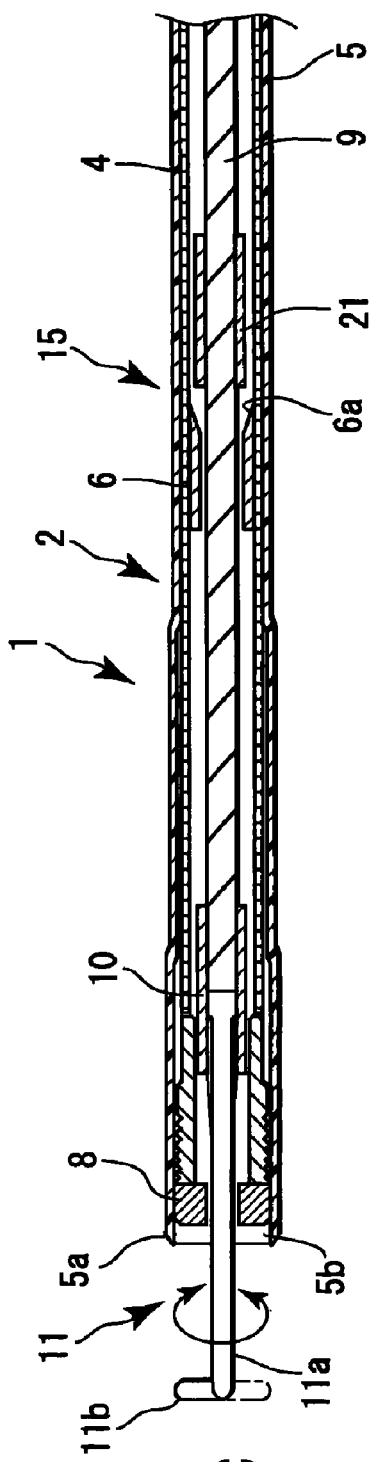

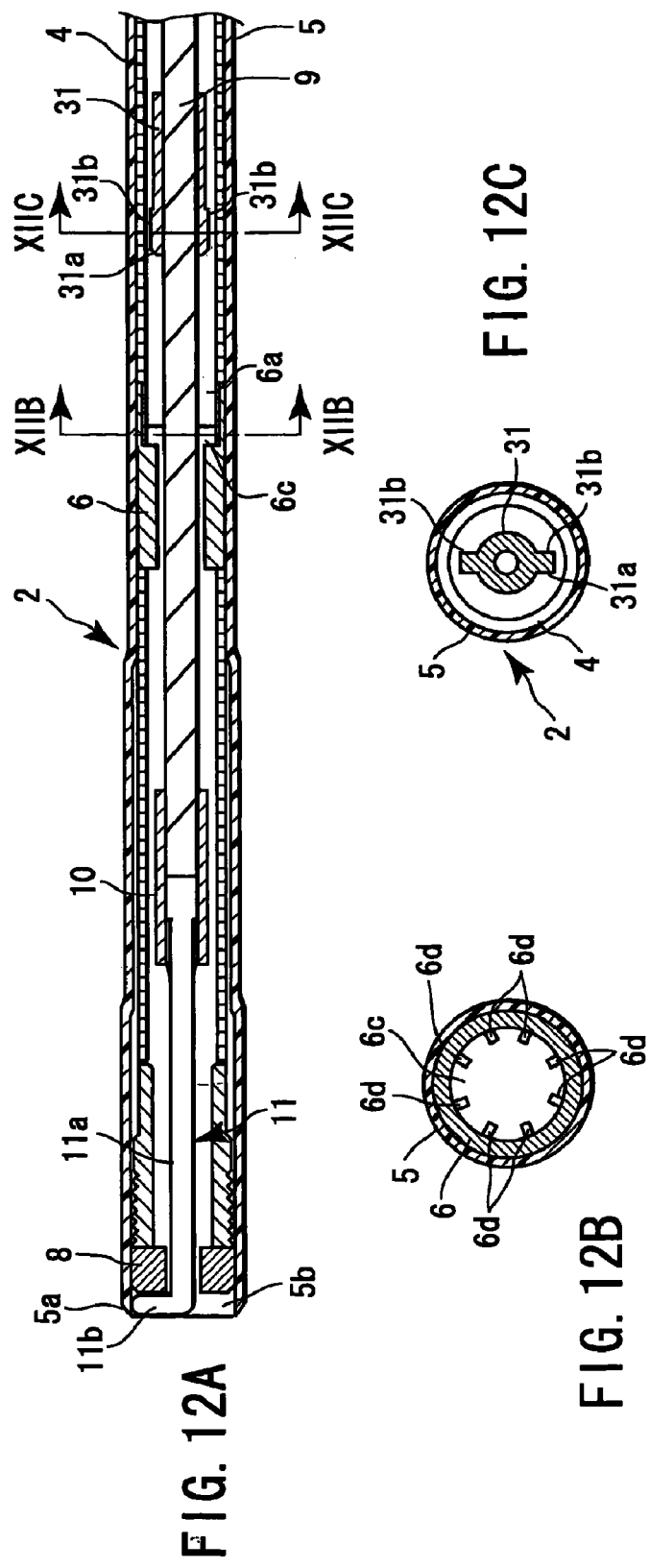

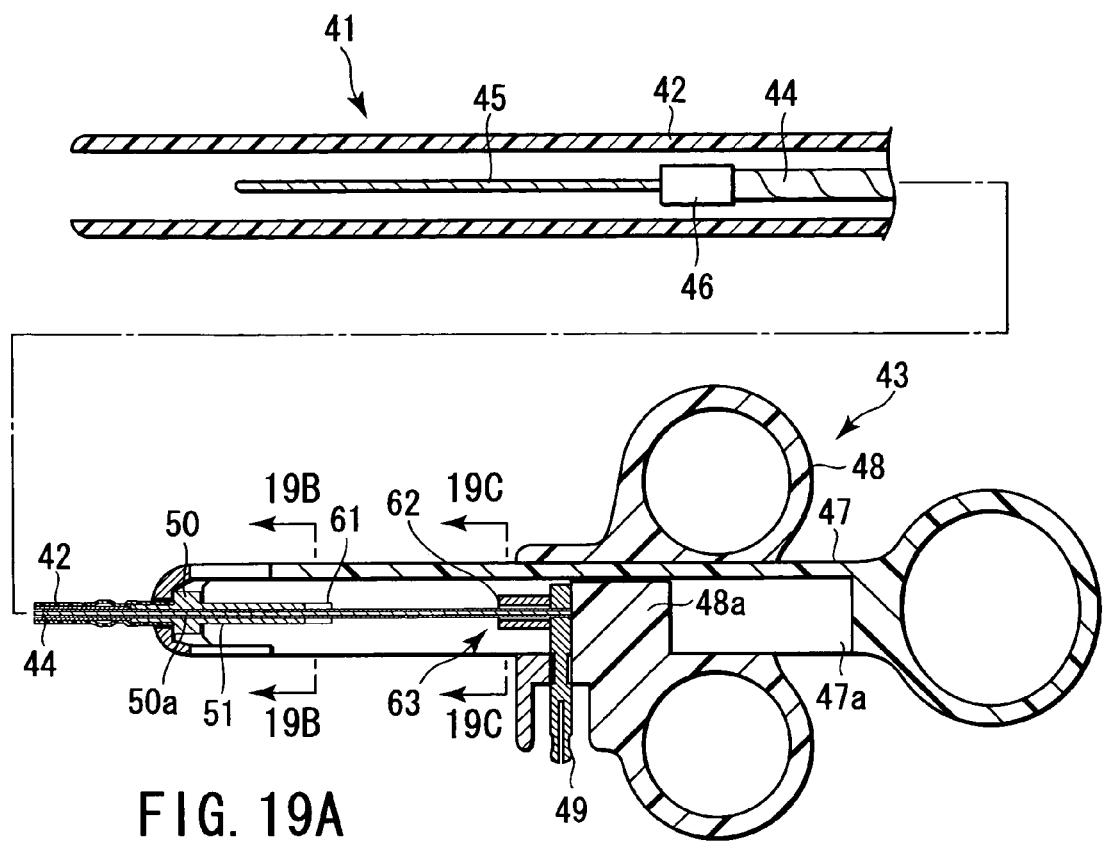
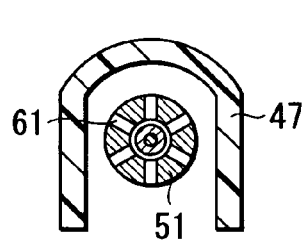 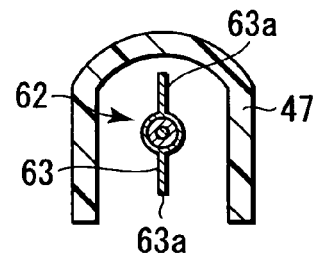
FIG. 19A
FIG. 19B
FIG. 19C

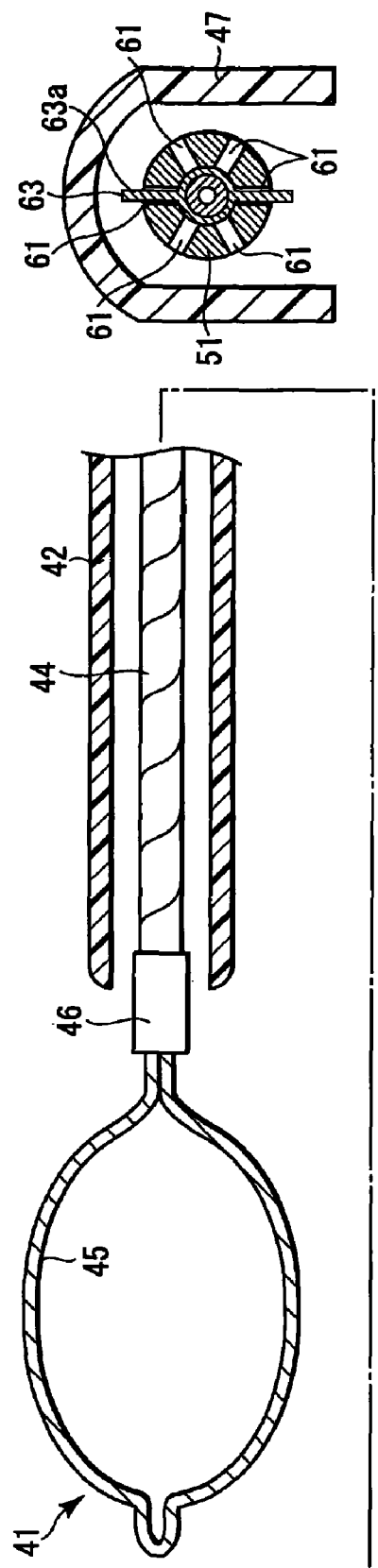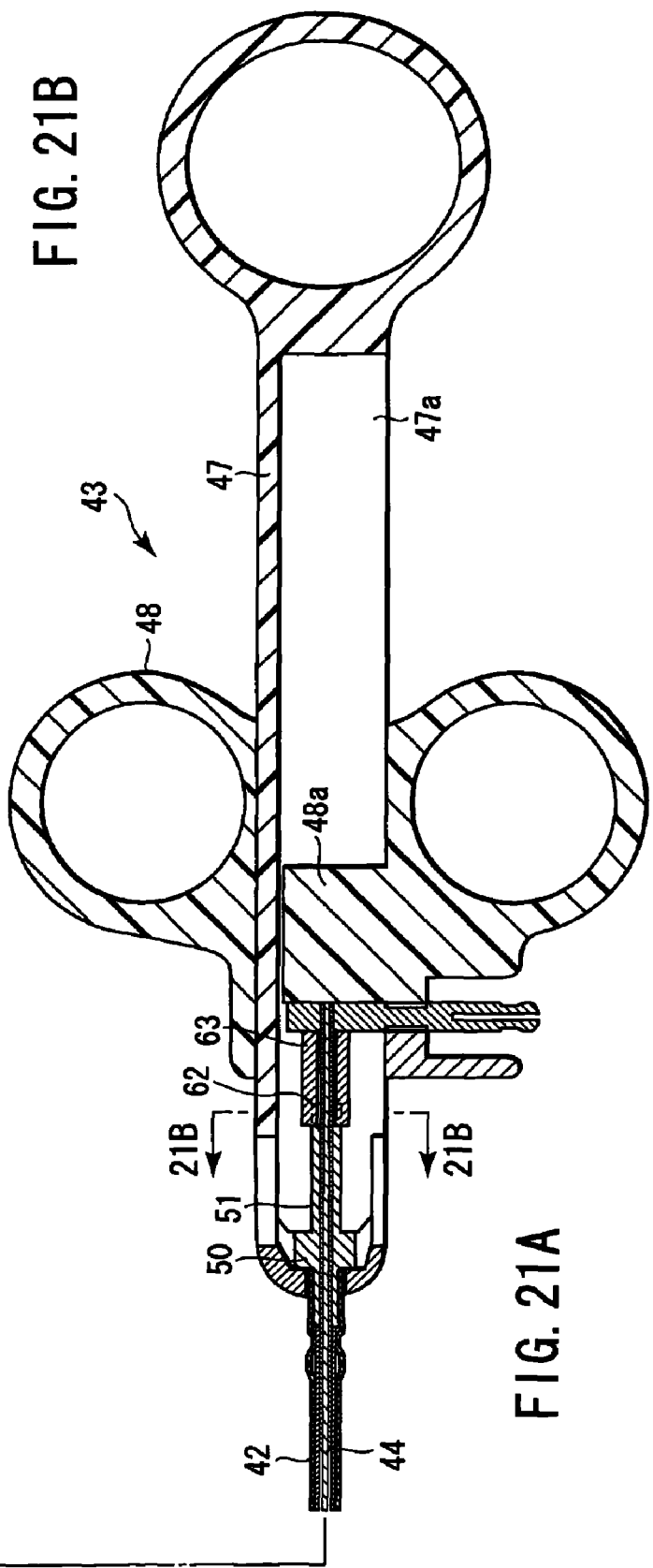

ENDOSCOPIC TREATMENT INSTRUMENT

CROSS-REFERENCE TO RELATED APPLICATIONS

This application is based upon and claims the benefit of priority from the prior Japanese Patent Application No. 2003-054644, filed Feb. 28, 2003, the entire contents of which are incorporated herein by reference.

BACKGROUND OF THE INVENTION

1. Field of the Invention

The present invention relates to an endoscopic treatment instrument such as a diathermic cutter for performing a resection treatment of resecting a living tissue.

2. Description of the Related Art

Conventionally, a treatment for resecting a living tissue, such as a mucous membrane, has been performed using an endoscopic treatment instrument, which is inserted into the body, for example, through the channel of an endoscope. In the treatment of resection, a diathermic (high-frequency) treatment instrument as disclosed, e.g. in Jpn. Pat. Appln. KOKAI Publication No. 62-50610 (Patent Document 1), is used.

The diathermic treatment instrument disclosed in Patent Document 1 has an elongated insertion section to be inserted in the channel of an endoscope, and an axially extending needle-like cutter section (electrode section) provided at a distal end portion of the elongated insertion section. In use, a high-frequency current is supplied to the cutter section. Thereby, a living tissue put in contact with the cutter section is cauterized and cut.

Jpn. Pat. Appln. KOKAI Publication No. 8-299355 (Patent Document 2) discloses a diathermic treatment instrument different from that of Patent Document 1. This diathermic treatment instrument has a ball-shaped electrical insulator at a distal end of the needle-like cutter section (electrode section).

Other diathermic treatment instruments with different structures are disclosed in Jpn. U. M. Appln. KOKAI Publication No. 60-184513 (Patent Document 3) and Tsuneo OYAMA et al. (six others), "Endoscopic Mucosal Resection Using a Hocking Knife", Stomach and Intestines, Aug. 2002, Vol. 37, No. 9, pp. 1155-1161 (Non-Patent Document 1). In these techniques, a bent portion to be hooked on a living tissue is provided at a distal end of the cutter section (electrode section), and while the living tissue hooked by the bent portion is being pulled up, it is cauterized and cut.

Jpn. Pat. Appln. KOKAI Publication No. 5-293118 (Patent Document 4) and Jpn. Pat. Appln. KOKAI Publication No. 8-126648 (Patent Document 5) disclose diathermic treatment instruments each having an outer tube and an insertion member to be inserted in the outer tube. A treatment section is provided at a distal end portion of the insertion member. A proximal-side portion of the insertion member to be inserted in the outer tube is rotated about its axis, whereby the entire insertion member is rotated about its axis. Thus, the rotation of the insertion member is transmitted to the distal-side treatment section, and the direction of the distal-side treatment section is changed.

The following operation is performed in resecting a living tissue using the diathermic treatment instrument disclosed in Patent Document 1. To start with, a to-be-resected part is punctured with a cutting section. The cutter section is then moved in a predetermined direction of resection. In many cases, the to-be-resected part is located on the surface side of the living tissue, and a tissue that is not to be resected is present in a deep region of the to-be-resected part. The surgeon is required to resect only the to-be-resected part. Therefore, the cutter section needs to be moved in the state in which the cutter section inserted in the to-be-resected part is kept at a constant depth. This prevents the cutter section, which is inserted in the to-be-resected part, from contacting the non-to-be-resected tissue located at a deep region of the to-be-resected part (i.e. from applying an electric effect on the non-to-be-resected tissue).

BRIEF SUMMARY OF THE INVENTION

The present invention may provide an endoscopic treatment instrument comprising:

a flexible sheath;

an operation member inserted in the sheath such that the operation member is axially slideable with respect to the sheath;

a treatment section provided at a distal end portion of the operation member and being slideable from/in the sheath;

a proximal-side operation section provided at a proximal end portion of the sheath, the operation section having a slider member, which slides the operation member in an axial direction of the sheath, and a rotation drive section which rotates the treatment section about the axis of the sheath; and a direction adjusting section which adjusts a direction of the treatment section, the direction adjusting section having a rotation restriction section which restricts rotation of the treatment section about an axis thereof, and the direction adjusting section moving the treatment section between a rotation restriction position where rotational restriction is effected by the rotation restriction section, and a restriction release position where the treatment section is made rotatable about the axis of the sheath relative to the sheath, in accordance with an advancing/retreating operation of the operation member by the slider member.

Preferably, the rotation restriction section includes a stopper member provided at a distal end portion of the sheath, and an abutment portion provided at a proximal end portion of the treatment section, the abutment portion detachably engaging the stopper member to make the treatment section unrotatable.

Preferably, the rotation restriction section includes an engaging mechanism which restricts rotation of the treatment section by a frictional force between a stopper member provided at a distal end portion of the sheath and an abutment portion provided at a proximal end portion of the treatment section.

Preferably, the engaging mechanism includes a mechanism which produces a frictional engaging force at a contact surface between the stopper member and the abutment portion by pushing forward the slider member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a vertical cross-sectional view of a main part, showing the state in which a cutter section of the diathermic cutter of the first embodiment is received in a sheath;

FIG. 2B is a vertical cross-sectional view of the main part, showing the state in which the cutter section of the diathermic cutter is projected out of the sheath;

FIG. 3A is a vertical cross-sectional view of the main part, illustrating an operation for rotating the cutter section of the diathermic cutter of the first embodiment about its own axis;

FIG. 3B is a vertical cross-sectional view of the main part, showing the state in which the cutter section of the diathermic cutter is shifted to a rotation restriction position;

FIG. 4A is a perspective view showing the state in which an initial cutting operation is performed to make a hole in a mucous membrane around a diseased mucous membrane part, when the diathermic cutter according to the first embodiment is used;

FIG. 4B is a perspective view showing the state in which a diathermic cutter is introduced into a body cavity via a channel of an endoscope;

FIG. 4C is a perspective view showing the state in which a distal end portion of the diathermic cutter is inserted in the hole made by the initial cutting operation;

FIG. 4D is a perspective view showing the state in which a cutting operation for the diseased mucous membrane part is performed by the cutter section;

FIG. 5A is a perspective view for explaining an operation for adjusting the direction of the bent portion of the cutter section of the diathermic cutter according to the first embodiment;

FIG. 5B is a perspective view for explaining an operation for cutting and resecting a lower layer of the diseased mucous membrane part by hooking the bent portion of the cutter section in the cut area made around the diseased mucous membrane part;

FIG. 8A is a vertical cross-sectional view of the main part, illustrating an operation of rotating the cutter section of the diathermic cutter according to the third embodiment about its axis;

FIG. 8B is a vertical cross-sectional view of the main part, showing the state in which the cutter section of the diathermic cutter is shifted to a rotation restriction position;

FIG. 9A is a vertical cross-sectional view of a main part, showing the retreated state in which a cutter section of a diathermic cutter according to a fourth embodiment of the invention is retreated in the sheath;

FIG. 9B is a cross-sectional view taken along line IXB-IXB in FIG. 9A;

FIG. 9C is a cross-sectional view taken along line IXC-IXC in FIG. 9A;

FIG. 9D is a vertical cross-sectional view of the main part, showing the state in which the cutter section of the diathermic cutter is projected out of the sheath;

FIG. 10A is a vertical cross-sectional view of the main part, illustrating an operation of rotating the cutter section of the diathermic cutter according to the fourth embodiment about its axis;

FIG. 10B is a vertical cross-sectional view of the main part, showing the state in which the cutter section of the diathermic cutter is shifted to a rotation restriction position;

FIG. 10C is a cross-sectional view taken along line XC-XC in FIG. 10B;

FIG. 11A is a vertical cross-sectional view of a main part, showing the retreated state in which a cutter section of a diathermic cutter according to a fifth embodiment of the invention is retreated in the sheath;

FIG. 11B is a vertical cross-sectional view of the main part, showing the state in which the cutter section of the diathermic cutter is projected out of the sheath;

FIG. 11C is a vertical cross-sectional view of the main part, illustrating an operation of rotating the cutter section of the diathermic cutter about its axis;

FIG. 12A is a vertical cross-sectional view of a main part, showing the retreated state in which a cutter section of a diathermic cutter according to a sixth embodiment of the invention is retreated in the sheath;

FIG. 12B is a cross-sectional view taken along line XIIB-XIIB in FIG. 12A;

FIG. 12C is a cross-sectional view taken along line XIIC-XIIC in FIG. 12A;

FIG. 12D is a vertical cross-sectional view of the main part, showing the state in which the cutter section of the diathermic cutter is projected out of the sheath;

FIG. 19A is a vertical cross-sectional view of a main part, showing the retreated state in which a snare loop of a diathermic snare according to an eighth embodiment of the invention is retreated in the sheath;

FIG. 19B is a cross-sectional view taken along line 19B-19B in FIG. 19A;

FIG. 19C is a cross-sectional view taken along line 19C-19C in FIG. 19A;

FIG. 21A is a vertical cross-sectional view of the main part, showing the state in which the snare loop of the diathermic snare according to the eighth embodiment is shifted to a rotation restriction position; and FIG. 21B is a cross-sectional view taken along line 21B-21B in FIG. 21A.

DETAILED DESCRIPTION OF THE INVENTION

Figure 1A:
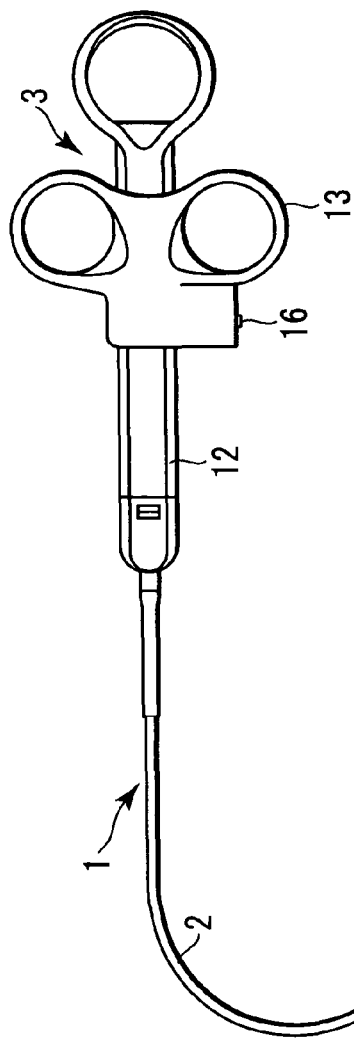
FIG. 1A is a vertical cross-sectional view of a main part, schematically showing the entire structure of a diathermic cutter according to a first embodiment of the present invention.

A first embodiment of the present invention will now be described with reference to FIG. 1A through FIG. 5B. FIG. 1A schematically shows the entire structure of a diathermic cutter 1 according to the first embodiment, which is an example of an endoscopic treatment instrument.

Figure 1B:
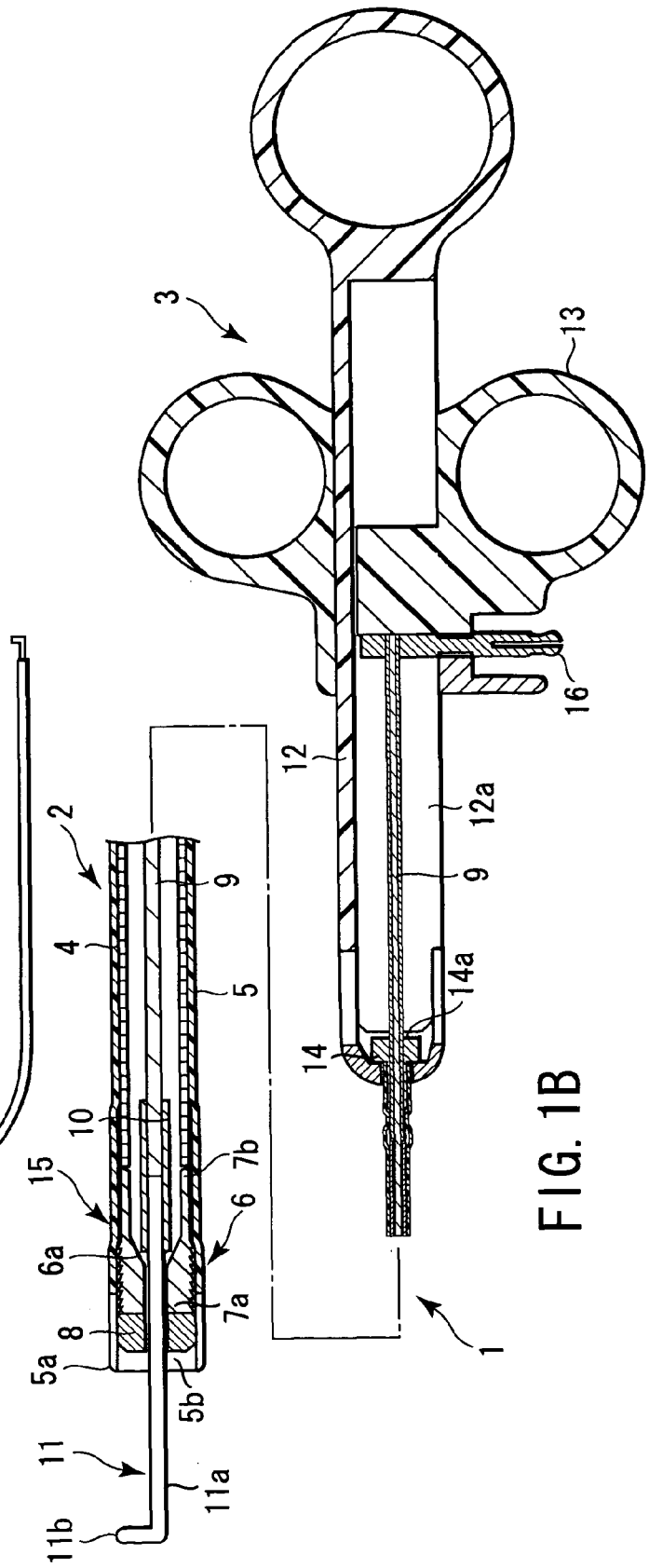
FIG. 1B is a vertical cross-sectional view of a main part, showing a distal portion and a proximal-side operation section of the diathermic cutter.

The diathermic cutter 1 comprises an elongated flexible sheath 2, and an operation section 3 provided at a proximal end of the sheath 2. The sheath 2 is insertable in the channel (not shown) of an endoscope. As is shown in FIG. 1B, the sheath 2 comprises, for instance, a densely-wound coil 4, and an insulation tube 5 that coats the outer periphery of the densely-wound coil 4. The insulation tube 5 is formed of, e.g. tetrafluoroethylene. A cylindrical stopper member 6 is coupled to a distal end portion of the densely-wound coil 4. A distal end portion of the insulation tube 5 extends to such a position as to cover the outer periphery of the stopper member 6. The outer periphery of the stopper member 6 is flush with the outer periphery of the densely-wound coil 4. The distal end portion of the insulation tube 5 is coated such that there is no stepped portion between the outer periphery of the stopper member 6 and the outer periphery of the densely-wound coil 4.

The stopper member 6 has a thick portion 7a at its distal end side and a thin portion 7b at its proximal end side. The thick portion 7a is formed such that it has a greater thickness than the thin portion 7b in a radially inward direction of the stopper member 6. Thereby, a large-diameter cavity portion is formed in the inside region of the thin region 7b at the proximal end side of the stopper member 6. In addition, an engaging recess portion 6a with a substantially conical taper surface is formed on the inner peripheral surface of the stopper member 6 between the thick portion 7a and thin portion 7b. Further, an annular insulation chip 8 for centering a cutter section 11 (to be described later) is provided at the distal end side of the thick portion 7a of the stopper member 6.

The inner peripheral surface of the insulation chip 8 has a diameter substantially equal to the diameter of the inner peripheral surface of the thick portion 7a. In other words, the inner peripheral surface of the insulation chip 8 is flush with the inner peripheral surface of the thick portion 7a without a stepped portion. Further, the outer periphery of the insulation chip 8 is covered with the insulation tube 5. As is shown in FIG. 1B, a distal end portion of the insulation tube 5 extends forward beyond the distal end of the insulation chip 8. An internal space of a distal-end extension portion 5a of the insulation tube 5 defines a receiving portion 5b of a bent portion 11b of the cutter section 11 (to be described later).

An electrically conductive operation wire (operation member) 9 is axially movably inserted in the sheath 2. An electrically conductive tubular stopper reception portion (abutment portion) 10, which is abutted upon the aforementioned stopper member 6, is attached to the distal end portion of the operation wire 9.

The cutter section (electrode section) 11 serving as a treatment section is connected to the stopper reception portion 10. The cutter section 11 is provided with a rod-shaped electrode portion 11a projecting axially from the distal end of the sheath 2. A bent portion 11b that is bent substantially at right angles is formed at the distal end portion of the rod-shaped electrode portion 11a. In this case, the cutter section 11 is formed of an electrically conductive material. A proximal end portion of the rod-shaped electrode portion 11a of the cutter section 11 is electrically connected to the stopper reception portion 10.

The operation section 3 of the diathermic cutter 1 includes a substantially shaft-shaped operation section body 12 and an operation slider (slider member) 13 that is axially slidable relative to the operation section body 12. A guide groove 12a for the operation slider 13 is axially provided on the operation section body 12. The operation slider 13 is so mounted as to be slidable along the guide groove 12a.

Further, a rotor (rotation means) 14 is provided at the proximal end portion of the sheath 2. The rotor 14 is rotatably connected to a front end portion of the operation section body 12. A passage hole 14a is formed at an axial center portion of the rotor 14. The operation wire 9 is passed through the passage hole 14a. A proximal end portion of the operation wire 9 passes through the passage hole 14a, extends rearwards, and is coupled to the operation slider 13. The operation wire 9 is axially advanced/retreated through the sheath 2 by the axial sliding operation of the operation slider 13. By the advancing/retreating operation of the operation wire 9, the cutter section 11 is projected/retreated from/in the distal end portion of the sheath 2. At this time, when the operation slider 13 is moved forward, the cutter section 11 is projected out of the sheath 2. The stopper reception portion 10 is abutted upon the stopper member 6, whereby the projecting operation of the cutter section 11 is stopped. An engaging mechanism (rotation restriction means) 15 for restricting the rotation of the cutter section 11 is constituted by a pressure-contact force caused by the abutment of the stopper reception portion 10 upon the stopper member 6.

A connector portion 16 is projectingly provided on the operation slider 13. A line (not shown) connected to a high-frequency generating device (not shown) is electrically connected to the connector portion 16.

An inner end portion of the connector portion 16 is electrically connected to the proximal end portion of the operation wire 9. Thereby, the cutter section 11 is electrically connected to the connector portion 16 of the operation slider 13 via the stopper reception portion 10 and operation wire 9. The cutter section 11 can be projected/retreated from/in the distal end portion of the sheath 2 by the advancing/retreating operation of the operation wire 9.

The operation of the diathermic cutter 1 according to the present embodiment with the above-described structure will now be described. To begin with, how to use the diathermic cutter 1 is described. When the diathermic cutter 1 is used, the operation slider 13 and operation section body 12 of the operation section 3 are grasped, as shown in FIG. 2A. If the operation slider 13 is moved backward (proximal side) relative to the operation section body 12, as shown in FIG. 2A by an arrow A1, the operation wire 9 is moved backward. Accordingly, the cutter section 11 is retreated in the sheath 2. At this time, the bent portion 11b of cutter section 11 is abutted upon the insulation chip 8 provided at the distal end of the sheath 2 and is accommodated in the receiving portion 5b. The bent portion 11b is generally held in this state when the cutter section 11 is not used, for example, at the time of insertion into the channel of the endoscope.

If the operation slider 13 is moved forward (distal end side) relative to the operation section body 12, as shown in FIG. 2B by an arrow A2, the operation wire 9 is moved forward. Accordingly, the cutter section 11 is projected out of the distal end of the sheath 2. At the time the stopper reception portion 10 abuts on the stopper member 6, the movement of the operation wire 9 is stopped (rotation restriction position).

When the direction of the bent portion 11b of the projected cutter section 11 is to be changed, the operation slider 13 is slightly moved backward relative to the operation section body 12, as shown in FIG. 3A by an arrow A3. Thereby, the stopper reception portion 10 is separated from the stopper member 6 (restriction release position). In this state, if the operation section 3 is rotated about its own axis with the sheath 2 being held, as shown in FIG. 3A by an arrow B1, the cutter section 11 is rotated at the same time about its own axis, as shown in FIG. 3A by an arrow B2. As a result, the direction of the bent portion 11b is changed.

At the time the bent portion 11b is turned in the desired direction, the operation slider 13 is moved forward relative to the operation section body 12, as shown in FIG. 3B by an arrow A4. After the stopper reception portion 10 abuts on the stopper member 6 and stops, the operation slider 13 is further pushed forward and the stopper reception portion 10 is pressed on the stopper member 6. The stroke of motion of the operation slider 13 provided on the operation section 3 is set to be longer than the distance of movement over which the stopper reception portion 10 moves and abuts on the stopper member 6. Thereby, the cutter section 11 is fixed in the state in which the bent portion 11b is set in the desired direction. Thus, the direction of the bent portion 11b is unchanged even if an external force acts on the cutter section 11. The cutter section 11 is used in this state when the cutter section 11 is supplied with electric power to resect a mucous membrane.

Next, referring to FIGS. 4A to 4D and FIGS. 5A and 5B, a description is given of the operation of resecting a mucous membrane in a body cavity, following the insertion of the diathermic cutter 1 into the body, for example, through the channel of the endoscope. To start with, an injector (not shown) is introduced into the body through the channel of the endoscope (not shown). Then, physiological saline is injected in a submucosa of a target diseased mucous membrane part H1 to be resected in the body cavity, and the diseased mucous membrane part H1 is raised, as shown in FIG. 4A.

Then, as shown in FIG. 4A, a publicly known diathermic cutter 17, as disclosed in, e.g. Patent Document 1, is introduced in the body through the channel of the endoscope (not shown). An initial cutting operation for making a hole H2 in a peripheral mucous membrane of the diseased mucous membrane part H1 is performed using the diathermic cutter 17.

Subsequently, as shown in FIG. 4B, a publicly known diathermic cutter 18 disclosed in Patent Document 2 is similarly introduced into the body cavity through the channel of the endoscope. A distal end portion of the diathermic cutter 18 is inserted in the hole H2 made by the initial cutting operation, as shown in FIG. 4C. In this state, while the diathermic cutter 18 is being supplied with high-frequency current, the cutter 18 is moved to cut a surrounding part of the diseased mucous membrane part H1, as indicated by an arrow in FIG. 4D. Thus, as shown in FIG. 5A, a cut area H3 is formed by cutting the surrounding part of the diseased mucous membrane part H1.

After the entire surrounding part of the diseased mucous membrane part H1 is cut, the diathermic cutter 1 according to the present embodiment is used. Prior to the introduction into the body cavity, the diathermic cutter 1 of this embodiment is set in the initial state in which the cutter section 11 is retreated in the sheath 2. In this state, the diathermic cutter 1 is introduced into the body cavity through the channel of the endoscope. Then, as shown in FIG. 5A, the cutter section 11 is put in contact with the cut area H3 formed by cutting the surrounding part of the diseased mucous membrane part H1. At this time, the bent portion 11b is hooked on the cut area H3, and the diathermic cutter 1 is moved in such a manner as to trace the cut area H3. Thus, the lower layer of the diseased mucous membrane part H1 is cut and resected. In this case, it is desirable that the bent portion 11b of the cutter section 11 be situated to be in parallel with a proper muscularis or to be directed to the lumen side.

In a case where the bent portion 11b is not situated in a desired direction, the direction of the bent portion 11b is adjusted by a method as illustrated in FIG. 3A and FIG. 3B. At the time of the direction adjusting work, the operation slider 13 of the operation section 3 is first slightly moved backward (in the direction of arrow A3 in FIG. 3A). Thus, the stopper reception portion 10 is separated from the stopper member 6 (restriction release position). In this state, the sheath 2 is held and the operation section 3 is rotated about its axis, as indicated by the arrow B1 in FIG. 3A. At this time, the cutter section 11 is simultaneously rotated about its axis, as indicated by the arrow B2 in FIG. 3A, and the direction of the bent portion 11b is changed.

At the time the bent portion 11b is turned in the desired direction, the operation slider 13 is moved forward, as indicated by arrow A4 in FIG. 3B. When the operation slider 13 is moved forward, the stopper reception portion 10 is abutted upon the stopper member 6 and the projecting motion of the cutter section 11 is stopped (rotation restriction position). At this time, the stopper reception portion 10 is strongly pushed on the taper face of the engaging recess portion 6a of stopper member 6. Thereby, the engaging mechanism 15 is activated. The rotation of the cutter section 11 is restricted by the pressure-contact force produced when the stopper reception portion 10 abuts on the stopper member 6. Accordingly, during the mucous membrane resection operation, the bent portion 11b of cutter section 11 is fixed in the desired direction. Thus, the mucous membrane resection operation can be safely performed.

After all the diseased mucous membrane part H1 is resected, the resected mucous membrane part H1 is held by grasping forceps (not shown) or the like. The resected mucous membrane part H1, along with the grasping forceps, is taken out through the channel of the endoscope. The resection treatment is thus completed.

The embodiment with the above structure has the following advantages. The diathermic cutter 1 of the present embodiment is provided with the engaging mechanism 15. According to the engaging mechanism 15, the operation wire 9 is advanced by the slider 13 and the stopper reception portion 10 of the operation wire 9 is abutted upon the stopper member 6 within the sheath 2. Thereby, the rotation of the bent portion 11b of the cutter section 11 is restricted. In addition, when the operation wire 9 is moved backward by the slider 13, the stopper reception portion 10 is pulled away from the stopper member 6. Thereby, the rotational restriction to the bent portion 11b of cutter section 11 is released, and the bent portion 11b of cutter section 11 is made rotatable about its axis relative to the sheath 2. After the direction of the bent portion 11b of cutter section 11 is desirably adjusted, the operation slider 13 is strongly pushed forward to activate the engaging mechanism 15. Thus, the adjusted direction of the bent portion 11b can be fixed. As a result, during the mucous membrane resection operation, the bent portion 11b can be kept in parallel with a proper muscularis or can be directed to the lumen side. Therefore, the mucous membrane resection operation can be safely performed.

Figure 6A:
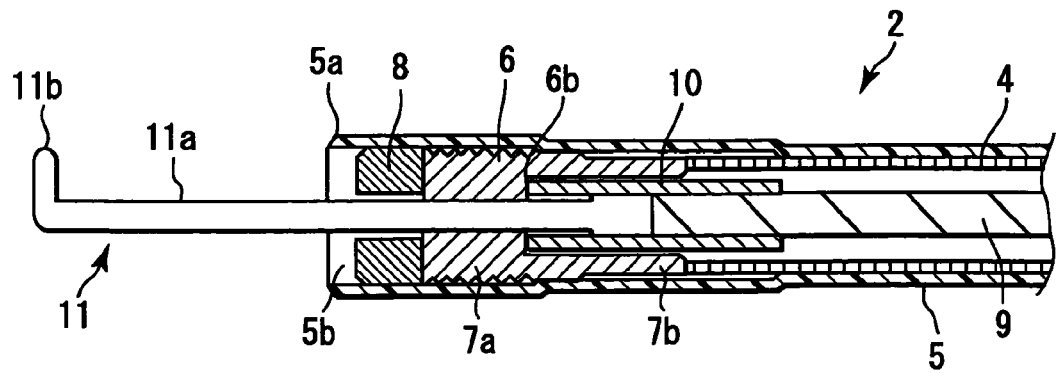
FIG. 6A is a vertical cross-sectional view of a main part, showing a distal-end portion of a diathermic cutter according to a second embodiment of the present invention.
Figure 6B:
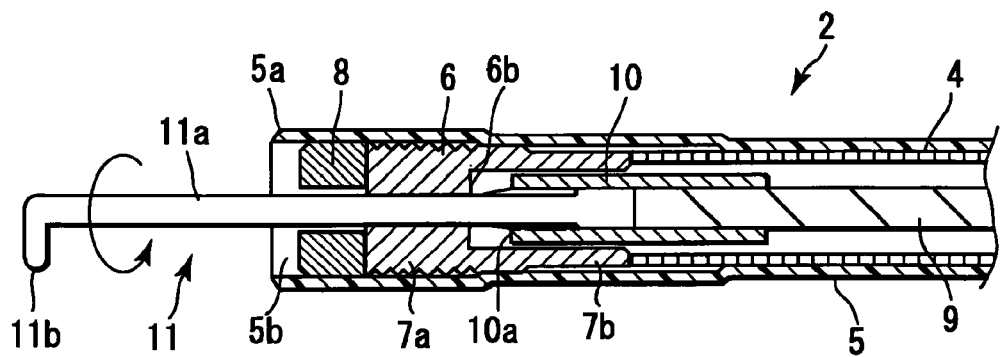
FIG. 6B is a vertical cross-sectional view of the main part, illustrating an operation of rotating a cutter section of the diathermic cutter about its axis.
Figure 6C:
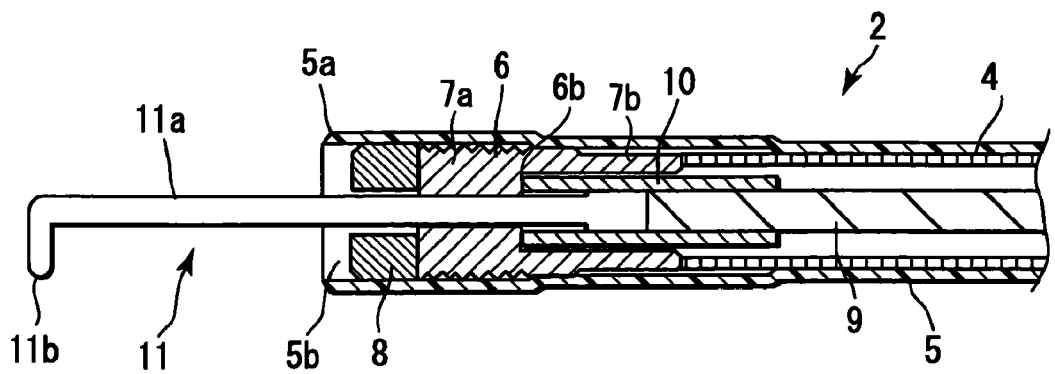
FIG. 6C is a vertical cross-sectional view of the main part, showing the state in which the cutter section of the diathermic cutter is shifted to a rotation restriction position.

FIG. 6A through FIG. 6C show a second embodiment of the present invention. In this embodiment, the structure of the diathermic cutter 1 according to the first embodiment (see FIG. 1A through FIG. 5B) is altered as described below. In the other respects, the structure of the second embodiment is the same as the diathermic cutter 1 of the first embodiment. The parts common to those of the diathermic cutter 1 of the first embodiment are denoted by like reference numerals, and a description thereof is omitted here.

In the diathermic cutter 1 of the first embodiment, the taper-shaped engaging recess portion 6a is provided on the cylindrical stopper member 6 between the thick portion 7a and thin portion 7b. On the other hand, in the diathermic cutter 1 of the second embodiment, the taper-shaped engaging recess portion 6a is replaced with a flat-face portion 6b, which is formed between the thick portion 7a and thin portion 7b and extends in a direction perpendicular to the axial direction. At the time the operation slider 13 is moved forward, a distal end face 10a of the stopper reception portion 10 is abutted upon the flat-face portion 6b of stopper member 6 in a surface-contact state. In this respect, the second embodiment differs from the first embodiment.

When the diathermic cutter 1 according to the present embodiment is operated, if the slider 13 is moved to advance the operation wire 9, the rotation of the bent portion 11b of the cutter section 11 is restricted by the frictional pressure contact force caused at the surface contact area between the distal end face 10a of stopper reception portion 10 and the flat-face portion 6b of stopper member 6.

The second embodiment with the above-described structure has the following advantages. In the second embodiment, when the slider 13 is advanced, the distal end face 10a of stopper reception portion 10 is put in surface-contact with the flat-face portion 6b of stopper member 6. Accordingly, the contact area between the stopper member 6 and stopper reception portion 10 can be increased. This increases the fixing force of the cutter section 11, which is obtained when the operation slider 13 is further pushed following the contact between the stopper member 6 and stopper reception portion 10.

The surface of the flat-face portion 6b of stopper member 6 is finished to be rough, like a matte-finished surface. In this case, the frictional pressure contact force between the distal end face 10a of stopper reception portion 10 and the flat-face portion 6b of stopper member 6 can be further increased, and the fixing portion of the cutter section 11 is increased.

FIG. 7A through FIG. 8B show a third embodiment of the present invention. In the third embodiment, the structure of the diathermic cutter 1 according to the first embodiment (see FIG. 1A through FIG. 5B) is altered as described below.

The diathermic cutter 1 of the present embodiment differs from the first embodiment only with respect to the structure of the stopper reception portion 10 of the operation wire 9. A distal end portion of the stopper reception portion 10 of the third embodiment is provided with a substantially conical taper surface lob. The taper surface 10b of the stopper reception portion 10 is formed to have a shape mating with the taper surface of the engaging recess portion 6a of the stopper member 6.

When the stopper reception portion 10 is put in contact with the stopper member 6, the taper surface 10b of the stopper reception portion 10 comes in surface-contact with the taper surface of the engaging recess portion 6a of the stopper member 6. The taper surface of the engaging recess portion 6a of stopper member 6 is smoothly finished, like a mirror surface. The taper surface 10b of the stopper reception portion 10 is similarly smoothly finished.

Figures 7A, 7B:
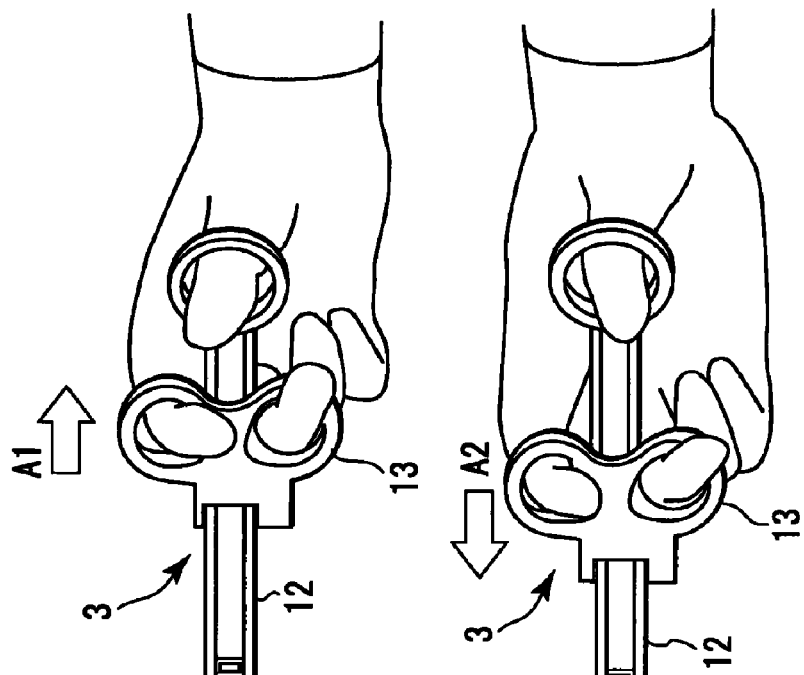
FIG. 7A is a vertical cross-sectional view of a main part, showing the retreated state in which a cutter section of a diathermic cutter according to a third embodiment of the invention is retreated in the sheath.
FIG. 7B is a vertical cross-sectional view of the main part, showing the state in which the cutter section of the diathermic cutter is projected out of the sheath.

The operation of the diathermic cutter 1 according to the third embodiment with the above structure will now be described. When the diathermic cutter 1 of this embodiment is used, the operation slider 13 is moved backward (toward the proximal end side) relative to the operation section body 12, as indicated by an arrow A1 in FIG. 7A. Thereby, the cutter section 11 is retreated in the sheath 2, as shown in FIG. 7A, and the bent portion 11b of the cutter section 11 is received in the receiving portion 5b. In this state, for example, the diathermic cutter 1 is inserted into the channel of the endoscope.

If the operation slider 13 is moved forward (to the distal end side) relative to the operation section body 12, as indicated by an arrow A2 in FIG. 7B, the cutter section 11 is projected out of the distal end of the sheath 2, as shown in FIG. 7B. At this time, the movement of the cutter section 11 is stopped in the state in which the taper surface 10b of stopper reception portion 10 is abutted upon the taper surface of the engaging recess portion 6a of stopper member 6. Thus, the direction of the bent portion 11b of the cutter section 11 is fixed at the desired position.

When the direction of the bent portion 11b of the projected cutter section 11 is to be changed, the operation slider 13 is slightly moved backward relative to the operation section body 12, from the state shown in FIG. 7B, as indicated by an arrow A3 in FIG. 8A. Thereby, the stopper reception portion 10 is separated from the stopper member 6 (restriction release position). In this state, the sheath 2 is held and the operation section 3 is rotated about its axis, as indicated by an arrow B1 in FIG. 8A. Thereby, the bent portion 11b of the cutter section 11 is rotated about its axis, as indicated by an arrow B2 in FIG. 8A, and the direction of the bent portion 11b is adjusted.

Subsequently, as indicated by an arrow A4 in FIG. 8B, the operation slider 13 is pushed forward to press the stopper reception portion 10 upon the stopper member 6. At this time, the taper surface 10b of the stopper reception portion 10 is put in surface-contact with the taper surface of the engaging recess portion 6a of the stopper member 6. Thus, the operation of projecting the cutter section 11 is stopped. In addition, the rotation of the cutter section 11 is restricted by the pressure-contact force caused by the abutment of the stopper reception portion 10 upon the stopper member 6, and the cutter section 11 is fixed. The other operational features are the same as those in the first embodiment.

The third embodiment with the above-described structure has the following advantages. In the third embodiment, the distal end portion of the stopper reception portion 10 has the taper surface lob. When the slider 13 is advanced, the taper surface 10b of the stopper reception portion 10 can be put in surface-contact with the taper surface of the engaging recess portion 6a of stopper member 6. As a result, the contact area between the stopper member 6 and stopper reception portion 10 can be increased, and the cutter section 11 can easily be fixed.

Furthermore, the taper surface of the engaging recess portion 6a of stopper member 6 and the taper surface 10b of the stopper reception portion 10 are smoothly finished. Accordingly, when the cutter section 11 is to be rotated about its axis, there is no need to pull the operation slider 13 to the proximal side and to separate the stopper reception portion 10 from the stopper member 6. Simply by rotating the operation section 3 about its axis, the cutter section 11 can be slid and rotated about its axis while keeping surface-contact between the taper surface of the engaging recess portion 6a of stopper member 6 and the taper surface 10b of the stopper reception portion 10. As a result, the work for adjusting the direction of the bent portion 11b of the cutter section 11 can more easily be performed. The other advantages are the same as those of the first embodiment.

FIG. 9A through FIG. 10C show a fourth embodiment of the present invention. In the fourth embodiment, the structures of the stopper member 6 and stopper reception portion 10 of the diathermic cutter 1 according to the first embodiment (see FIG. 1A through FIG. 5B) are altered as described below.

As is shown in FIG. 9A, in the diathermic cutter 1 of this embodiment, a substantially annular engaging hole 6c is provided at a bottom part of the engaging recess portion 6a of stopper member 6 (i.e. at a thick portion (7a)-side end of the engaging recess portion 6a). As is shown in FIG. 9B, in the engaging hole 6c, a plurality of projections 6d, which extend radially inward, are circumferentially arranged on the inner peripheral surface of the engaging recess portion 6a.

In addition, as shown in FIG. 9A, a wing-like engaging portion 10c is provided at the distal end of the stopper reception portion 10. Specifically, as shown in FIG. 9C, the engaging portion 10c has a pair of projection portions 10d projecting from the outer peripheral surface of the stopper reception portion 10. Each projection portion 10d is selectively fitted between any one of pairs of adjacent projections 6d provided in the engaging hole 6c of stopper member 6.

The operation of the fourth embodiment with the above structure is described. When the diathermic cutter 1 of this embodiment is used, the operation slider 13 is moved backward (toward the proximal end side) relative to the operation section body 12, as indicated by an arrow A1 in FIG. 9A. Thereby, the cutter section 11 is retreated in the sheath 2, as shown in FIG. 9A, and the bent portion 11b of the cutter section 11 is received in the receiving portion 5b. In this state, for example, the diathermic cutter 1 is inserted into the channel of the endoscope.

If the operation slider 13 is moved forward (to the distal end side) relative to the operation section body 12, as indicated by an arrow A2 in FIG. 9D, the cutter section 11 is projected out of the distal end of the sheath 2. At this time, the distal end of the stopper reception portion 10 is inserted into the engaging recess portion 6a. Just before the paired projection portions 10d of the stopper reception portion 10 are fitted in the engaging hole 6c of stopper member 6, the projection portions 10d abut on some projections 6d in the engaging hole 6c and stop at this position. In this state, as indicated by an arrow B1 in FIG. 10A, the operation section 3 is rotated about its axis relative to the sheath 2, and the bent portion 11b of the cutter section 11 is rotated about its axis, as indicated by an arrow B2 in FIG. 10A. Thus, the direction of the bent portion 11b is adjusted in a desired direction.

Subsequently, the operation slider 13 is further pushed forward, as indicated by an arrow A4 in FIG. 10B, and thus the distal end portion of the stopper reception portion 10 is fitted in the engaging hole 6c of the stopper member 6. At this time, as shown in FIG. 10C, the paired projection portions 10d of the engaging portion 10c of stopper reception portion 10 are engaged with the associated projections 6d in the engaging hole 6c of stopper member 6, and the rotation of the projection portions 10d is restricted. Accordingly, the rotation of the stopper reception portion 10 relative to the stopper member 6 is prevented. As a result, the rotation of the cutter section 11 is prevented, and the bent portion 11b is kept in the desired direction. In the other respects, the fourth embodiment is the same as the third embodiment.

According to the diathermic cutter 1 of this embodiment with the above structure, the operation wire 9 is advanced by the slider 13 and the stopper reception portion 10 provided at the distal end of the operation wire 9 is abutted upon the stopper member 6 within the sheath 2. In this case, the paired projection portions 10d of the stopper reception portion 10 are fitted between the projections 6d in the engaging hole 6c. Thereby, the rotation of the bent portion 11b of the cutter section 11 is restricted. When the operation wire 9 is moved backward by the slider 13 and the stopper reception portion 10 is separated from the stopper member 6, the rotational restriction to the bent portion 11b of the cutter section 11 is released and the bent portion 11b of the cutter section 11 is permitted to rotate about its axis relative to the sheath 2. Like the first embodiment, after the bent portion 11b of cutter section 11 is adjusted in the desired direction, the operation slider 13 is pushed forward. Thereby, the direction of the bent portion 11b is fixed. As a result, during the mucous membrane resection operation, the bent portion 11b can be kept in parallel with a proper muscularis or can be directed to the lumen side. Therefore, the mucous membrane resection operation can be safely performed.

FIGS. 11A to 11D show a fifth embodiment of the present invention. In the fifth embodiment, the structure of the engaging mechanism 15 for restricting the rotation of the cutter section 11 of the diathermic cutter 1 according to the first embodiment (see FIG. 1A through FIG. 5B) is altered as described below.

In the diathermic cutter 1 of this embodiment, as shown in FIG. 11A, the stopper member 6 of the engaging mechanism 15 is spaced apart backward from the position of the insulation chip 8. That is, the stopper member 6 is fixedly situated at a middle part of the sheath 2.

In addition, a tubular second stopper reception portion 21, which is to be abutted upon the stopper member 6, is provided at a position spaced apart rearward from the stopper reception portion 10 provided at the distal end of the operation wire 9. In the other structural features, the fifth embodiment is the same as the first embodiment.

The operation of the fifth embodiment with the above-described structure is described. When the diathermic cutter 1 of this embodiment is used, the same operation as with the first embodiment is performed. For example, as shown in FIG. 11A, the diathermic cutter 1 is inserted into the channel of the endoscope in the state in which the bent portion 11b of the cutter section 11 is received in the receiving portion 5b.

In this state, the operation slider 13 shown in FIG. 1B is moved forward (to the distal end side) relative to the operation section body 12. Thereby, as shown in FIG. 11B, the cutter section 11 is projected out of the distal end of the sheath 2. In this case, at the time the second stopper reception portion 21 abuts on the stopper member 6, the movement of the operation wire 9 is stopped (rotation restriction position).

Figure 11D:
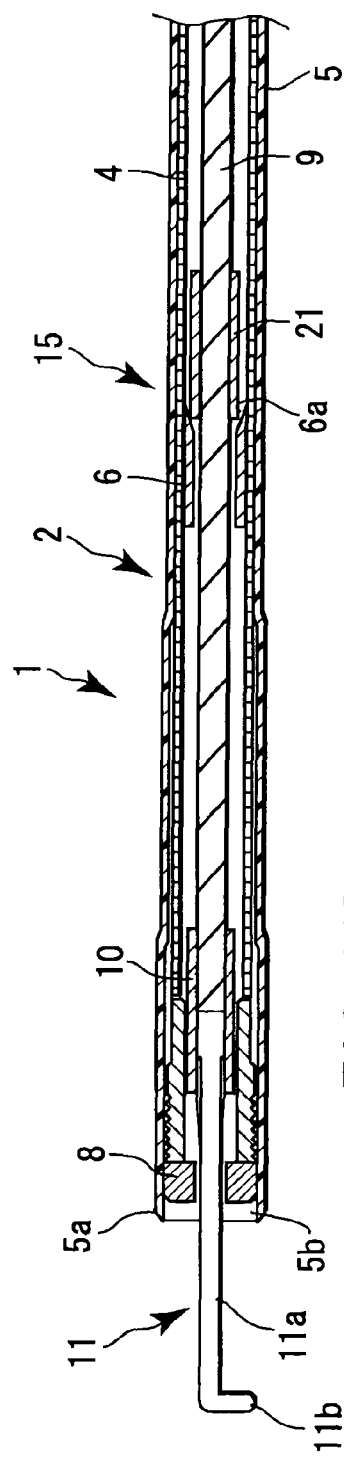
FIG. 11D is a vertical cross-sectional view of the main part, showing the state in which the cutter section of the diathermic cutter is shifted to a rotation restriction position.

Then, the operation slider 13 is slightly pulled backward, and the second stopper reception portion 21 is separated from the stopper member 6, as shown in FIG. 11C (restriction release position). In this state, the operation section 3 is rotated about its axis to adjust the direction of the bent portion 11b. Subsequently, as shown in FIG. 11D, the operation slider 13 is pushed forward and the second stopper reception portion 21 is pressed on the stopper member 6. Thereby, the cutter section 11 is fixed in the state in which the bent portion 11b is kept in the desired direction. In the other respects, the fifth embodiment is the same as the first embodiment.

According to the diathermic cutter 1 of this embodiment, like the first embodiment, after the bent portion 11b of the cutter section 11 is adjusted in the desired direction, the operation slider 13 is strongly pushed forward, whereby the direction of the bent portion 11b can be fixed. During the mucous membrane resection operation, the bent portion 11b can be kept in parallel with a proper muscularis or can be directed to the lumen side. Therefore, the mucous membrane resection operation can be safely performed.

FIG. 12A through FIG. 13C show a sixth embodiment of the present invention. In the sixth embodiment, the structure of the engaging mechanism 15 for restricting the rotation of the cutter section 11 of the diathermic cutter 1 according to the fifth embodiment (see FIGS. 11A to 11D) is replaced with the structure of the fourth embodiment (see FIG. 9A through FIG. 10C).

In the sixth embodiment, as shown in FIG. 12A, the stopper member 6 of the engaging mechanism 15 is spaced apart backward from the position of the insulation chip 8. That is, the stopper member 6 is fixedly situated at a middle part of the sheath 2. A substantially annular engaging hole 6c is provided at a bottom part of the engaging recess portion 6a of stopper member 6 (i.e. at a thick portion (7a)-side end of the engaging recess portion 6a). As is shown in FIG. 12B, a plurality of projections 6d, which extend radially inward, are circumferentially arranged on the inner peripheral surface of the engaging hole 6c.

In addition, in this embodiment, a tubular second stopper reception portion 31, which is to be abutted upon the stopper member 6, is provided at a position spaced apart rearward from the stopper reception portion 10 provided at the distal end of the operation wire 9. A wing-like engaging portion 31a is provided at the distal end of the second stopper reception portion 31. Specifically, as shown in FIG. 12C, the engaging portion 31a has a pair of projection portions 31b projecting from the outer peripheral surface of the second stopper reception portion 31. Each projection portion 31b is selectively fitted between any one of pairs of adjacent projections 6d provided in the engaging hole 6c of stopper member 6. In the other respects, the sixth embodiment is the same as the fifth embodiment.

The operation of the sixth embodiment with the above structure is described. When the diathermic cutter 1 of this embodiment is used, as shown in FIG. 12A, for example, the diathermic cutter 1 is inserted into the channel of the endoscope in the state in which the bent portion 11b of the cutter section 11 is received in the receiving portion 5b.

In this state, the operation slider 13 is moved forward, and, as shown in FIG. 12D, the cutter section 11 is projected out of the distal end of the sheath 2. At this time, the distal end of the second stopper reception portion 31 is inserted into the engaging recess portion 6a. Just before the paired projection portions 31b of the second stopper reception portion 31 are fitted in the engaging hole 6c of stopper member 6, the projection portions 31b abut on some projections 6d in the engaging hole 6c and stop at this position. In this state, the operation section 3 is rotated about its axis relative to the sheath 2, and the bent portion 11b of the cutter section 11 is rotated about its axis. Thus, the direction of the bent portion 11b is adjusted in a desired direction.

Figure 13A:
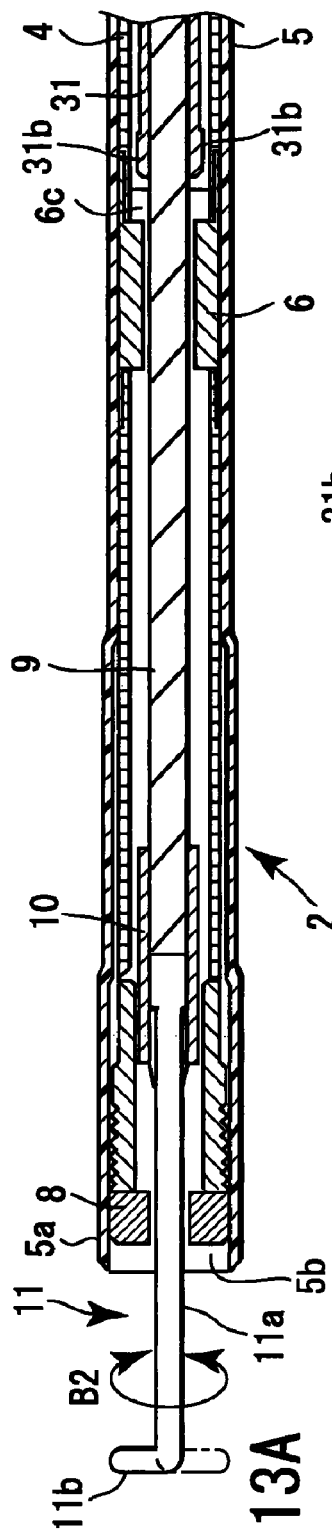
FIG. 13A is a vertical cross-sectional view of the main part, illustrating an operation of rotating the cutter section of the diathermic cutter according to the sixth embodiment about its axis.
Figure 13C:
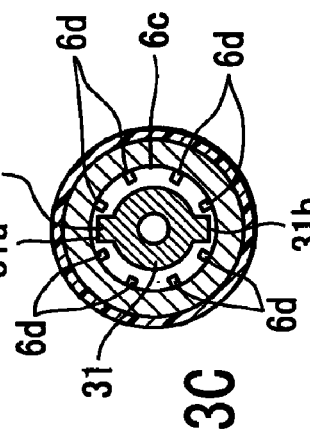
FIG. 13C is a cross-sectional view taken along line XIIIC-XIIIC in FIG. 13B.
Figure 13B:
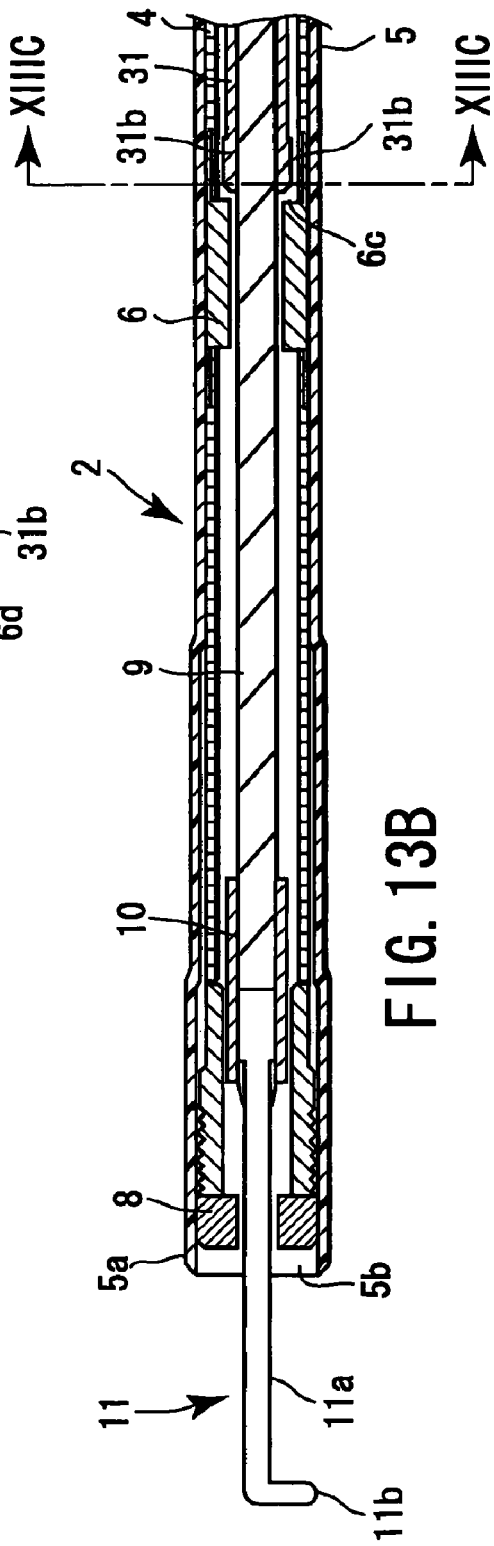
FIG. 13B is a vertical cross-sectional view of the main part, showing the state in which the cutter section of the diathermic cutter is shifted to a rotation restriction position.

Subsequently, the operation slider 13 is further pushed forward, and thus the distal end portion of the second stopper reception portion 31 is fitted in the engaging hole 6c of the stopper member 6, as shown in FIG. 13B. At this time, as shown in FIG. 13C, the paired projection portions 31b of the second stopper reception portion 31 are engaged with the associated projections 6d in the engaging hole 6c, and the rotation of the projection portions 31b is restricted. Accordingly, the rotation of the second stopper reception portion 31 relative to the stopper member 6 is prevented. As a result, the rotation of the cutter section 11 is prevented, and the bent portion 11b is kept in the desired direction. In the other respects, the sixth embodiment is the same as the fifth embodiment.

According to the diathermic cutter 1 of this embodiment with the above structure, the operation wire 9 is advanced by the slider 13 and the second stopper reception portion 31 of the operation wire 9 is abutted upon the stopper member 6 within the sheath 2. In this case, the paired projection portions 31b of the second stopper reception portion 31 are fitted between the projections 6d in the engaging hole 6c. Thereby, the rotation of the bent portion 11b of the cutter section 11 is restricted. When the operation wire 9 is moved backward by the slider 13 and the second stopper reception portion 31 is separated from the stopper member 6, the rotational restriction to the bent portion 11b of the cutter section 11 is released and the bent portion 11b of the cutter section 11 is permitted to rotate about its axis relative to the sheath 2. Like the first embodiment, after the bent portion 11b of cutter section 11 is adjusted in the desired direction, the operation slider 13 is pushed forward. Thereby, the direction of the bent portion 11b is fixed. As a result, during the mucous membrane resection operation, the bent portion 11b of cutter section 11 can be kept in parallel with a proper muscularis or can be directed to the lumen side. Therefore, the mucous membrane resection operation can be safely performed.

Figure 14:
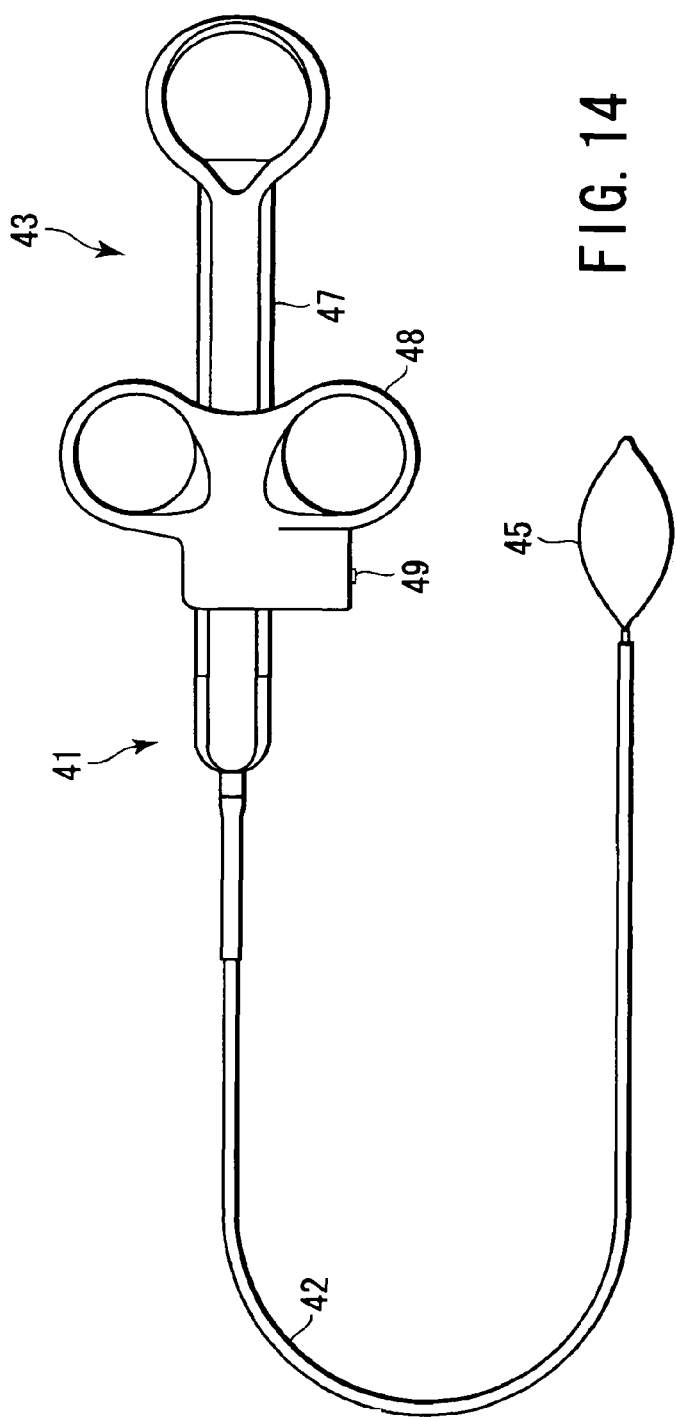
FIG. 14 is a side view schematically showing the entire structure of a diathermic snare according to a seventh embodiment of the invention.

FIGS. 14 to 18 show a seventh embodiment of the present invention. In this embodiment, the diathermic cutter 1 of the first embodiment (see FIG. 1A through FIG. 5B), which serves as the endoscopic treatment instrument, is replaced with a diathermic snare 41. FIG. 14 schematically shows the entire structure of the diathermic snare 41 of the seventh embodiment.

The diathermic snare 41 comprises an elongated flexible sheath 42 and an operation section 43 provided at a proximal end of the sheath 42. The sheath 42 is insertable in the channel of an endoscope (not shown). The sheath 42 is formed of an electrically insulating tube of, e.g. tetrafluoroethylene.

Figure 15:
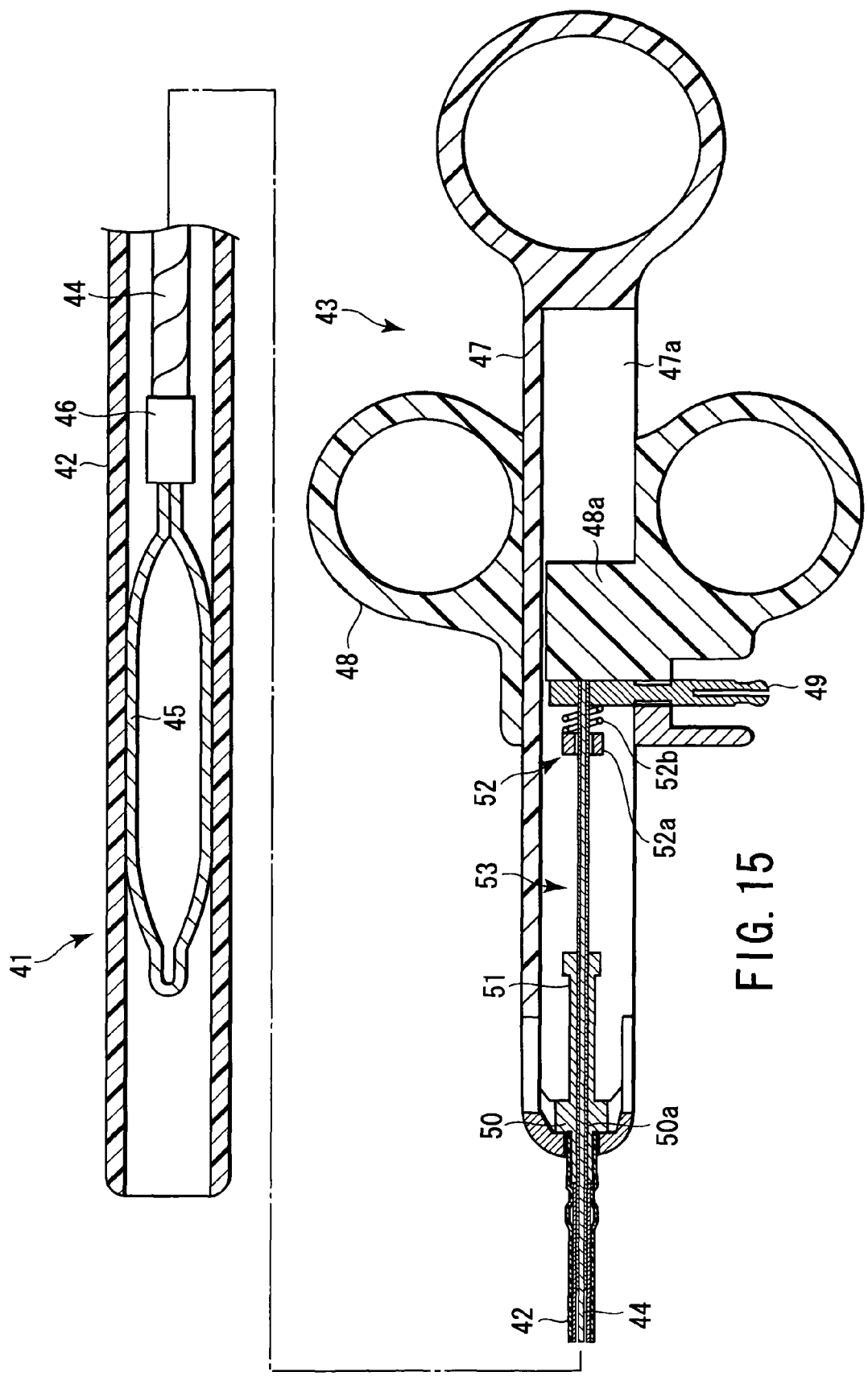
FIG. 15 is a vertical cross-sectional view of a main part, showing the retreated state in which a snare loop of a diathermic snare according to the seventh embodiment is retreated in the sheath.
Figure 16:
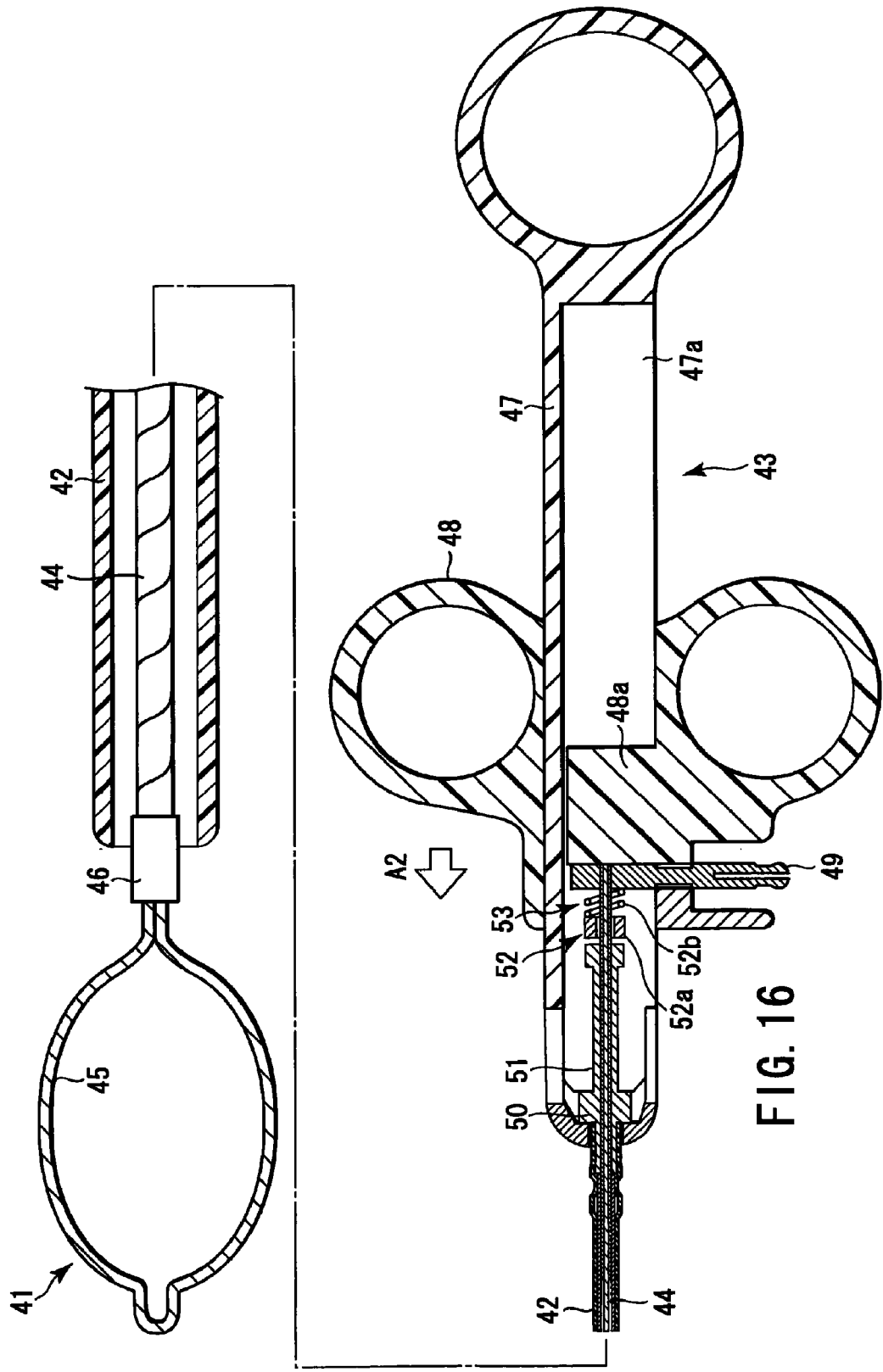
FIG. 16 is a vertical cross-sectional view of the main part, showing the state in which the snare loop of the diathermic snare according to the seventh embodiment is projected out of the sheath.

As is shown in FIG. 15, an electrically conductive operation wire 44 is axially movably inserted in the sheath 42. A snare loop 45, which is formed by folding a conductive wire, is coupled to the distal end of the operation wire 44 by means of a coupling member 46. The snare loop 45 has a self-opening capability. When the snare loop 45 projects from the sheath 42, as shown in FIG. 16, it expands in a loop shape.

The operation section 43 includes a shaft-shaped operation section body 47 and a substantially cylindrical slider 48 that is axially advanceable/retreatable along the operation section body 47. The operation section body 47 is provided with an axially extending guide groove 47a. A projection portion 48a, which projects inward and is inserted in the guide groove 47a, is provided on the inner peripheral surface of the slider 48. The slider 48 is axially slidably mounted on the operation section body 47 in the state in which the projection portion 48a can axially be guided along the guide groove 47a.

The slider 48 is provided with a connector section 49 that projects in a direction perpendicular to the axial direction. An outer end portion of the connector section 49 is electrically connected to a line (not shown) connected to a high-frequency generating device (not shown). As is shown in FIG. 15, an inner end portion of the connector section 49 is electrically connected to a proximal end portion of the operation wire 44. Thereby, the snare loop 45 is electrically connected to the connector section 49 of slider 48 via the coupling member 46 and operation wire 44.

A proximal end portion of the sheath 42 is provided with a rotor (rotation means) 50. The rotor 50 is rotatably connected to a front end portion of the operation section body 47. A proximal end portion of the rotor 50 is provided with a tubular stopper member 51 that extends rearward.

Further, a passage hole 50a for passage of the operation wire 44 is formed in an axial center portion of the rotor 50. The proximal end portion of the operation wire 44 is passed through the passage hole 50a in the rotor 50 and a tubular hole in the stopper member 51, extended rearward, and coupled to the slider 48.

A stopper reception portion 52 is provided at an axial center portion of the slider 48. The stopper reception portion 52 is fixed to the distal end of the projection portion 48a of slider 48. The stopper reception portion 52 comprises an annular reception portion body 52a and a spring member 52b. The spring member 52b is provided between the reception portion body 52a and the projection portion 48a of slider 48. The proximal end portion of the operation wire 44 is passed through the reception portion body 52a and spring member 52b and coupled to the slider 48.

When the slider 48 is axially slid, the operation wire 44 is axially advanced/retreated through the sheath 42. In accordance with the advancing/retreating operation of the operation wire 44, the snare loop 45 is projected/retreated from/into the distal end of the sheath 42. In this case, if the slider 48 is advanced to the distal end side relative to the operation section body 47, the snare loop 45 is projected from the flexible sheath 42, as shown in FIG. 16. The snare loop 45, projected from the flexible sheath 42, opens in a substantially oval shape by its own self-opening capability. On the other hand, if the slider 48 is retreated relative to the operation section body 47, the snare loop 45 is pulled and received in the flexible sheath 42 while being contracted.

When the slider 48 is moved forward and advanced, the stopper reception portion 52 abuts on the stopper member 51 and the operation of projecting the snare loop 45 is stopped. In this case, after the reception portion body 52a abuts on the stopper member 51 and stops, the slider 48 is further advanced so that the spring member 52b is compressed and the reception portion body 52a is pressed on the stopper member 51. Thereby, an engaging mechanism (rotation restriction means) 53, which restricts the rotation of the snare loop 45 by a pressure-contact force caused by the abutment of the stopper reception portion 52 upon the stopper member 51, is constituted.

The operation of the diathermic snare 41 of this embodiment will now be described. To begin with, how to use the diathermic snare 41 is described. FIG. 15 shows the state in which the slider 48 of the operation section 43 is moved backward (to the proximal side) relative to the operation section body 47. In this state, the operation wire 44 is moved rearward and accordingly the snare loop 45 is pulled in the sheath 42. The diathermic snare 41 is generally set in this state when the snare loop 45 is not used, for example, when the diathermic snare 41 is inserted in the channel of the endoscope.

In the state shown in FIG. 15, the slider 48 is moved forward (to the distal end side) relative to the operation section body 47, as indicated by an arrow A2 in FIG. 16. The operation wire 44 is thus moved forward. At this time, the snare loop 45 is pushed forward by the operation wire 44. As a result, the snare loop 45 is projected out of the distal end of the sheath 42 and it opens in a substantially oval shape. At the time the reception portion body 52a abuts on the stopper 51, the movement of the operation wire 44 stops (rotation restriction position).

Figure 17:
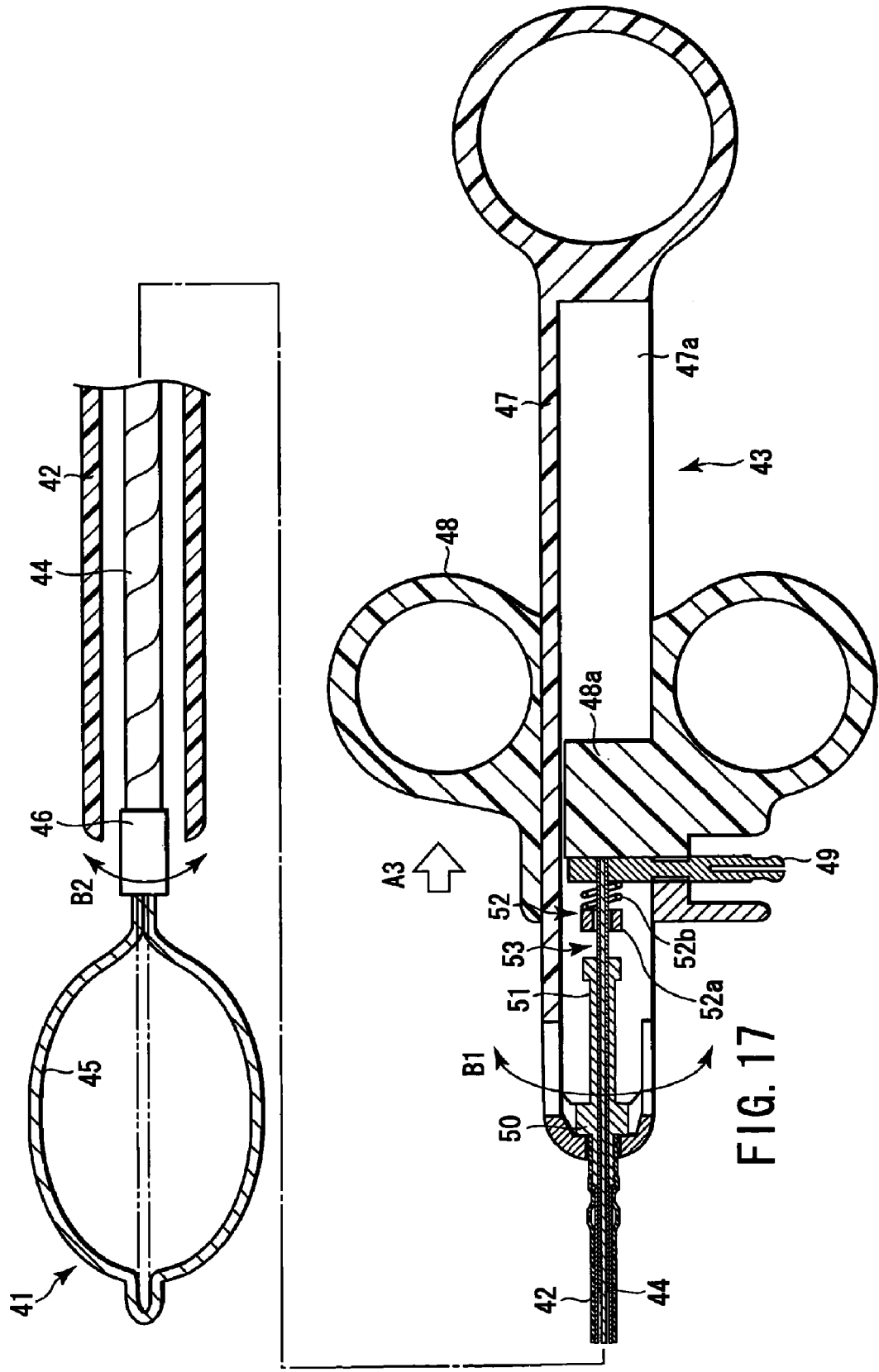
FIG. 17 is a vertical cross-sectional view of the main part, illustrating an operation of rotating the snare loop of the diathermic snare according to the seventh embodiment about its axis.

When the direction of the projected snare loop 45 is to be changed, the slider 48 in the state shown in FIG. 16 is slightly moved backward relative to the operation section body 47, as indicated by an arrow A3 in FIG. 17. Thereby, the reception portion body 52a moves away from the stopper member 51 (restriction release position). In this state, the sheath 42 is held and the operation section 43 is rotated about its axis, as indicated by an arrow B1 in FIG. 17. Accordingly, the snare loop 45 is rotated about its axis, as indicated by an arrow B2 in FIG. 17, and the direction of the snare loop 45 is changed.

Figure 18:
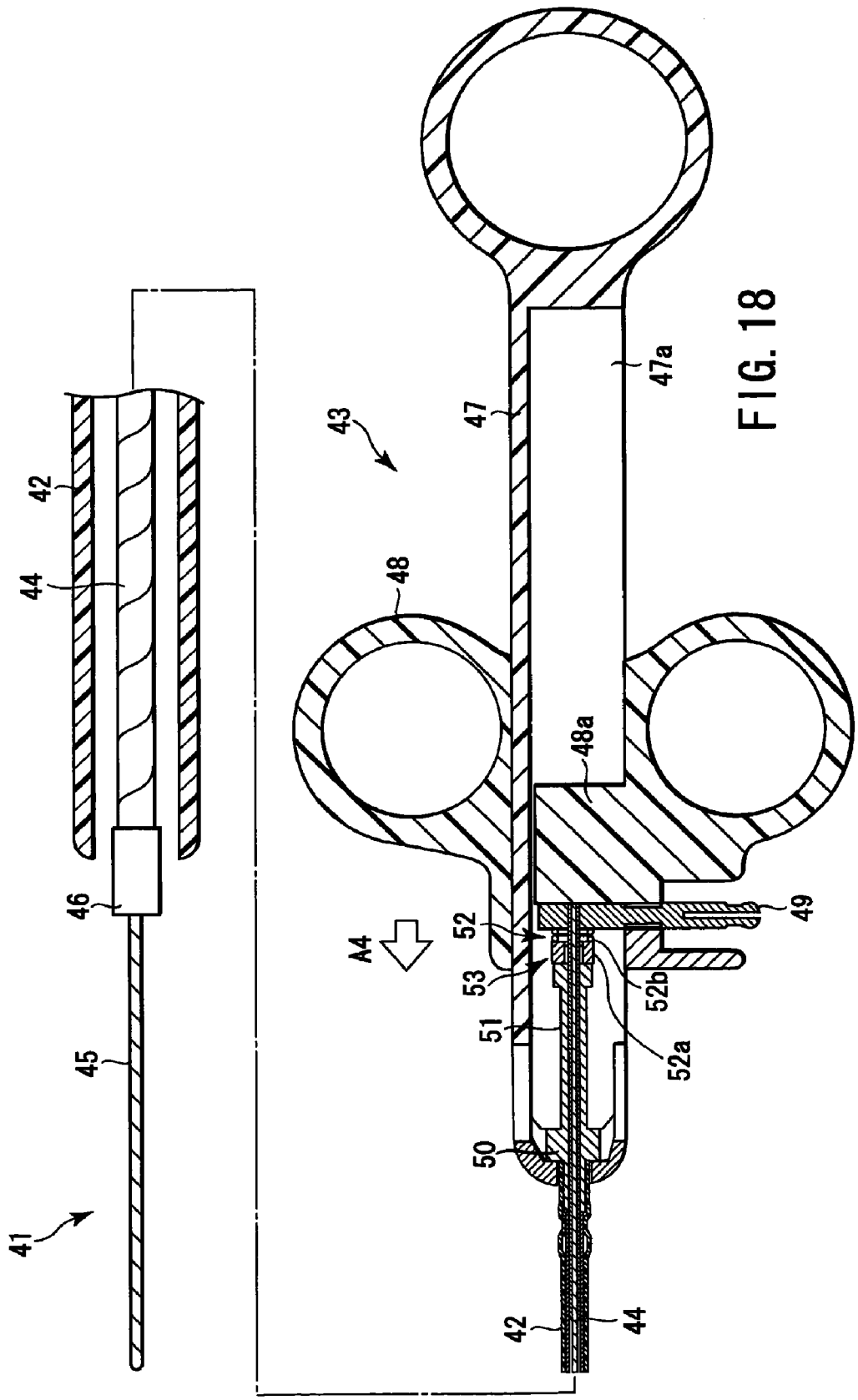
FIG. 18 is a vertical cross-sectional view of the main part, showing the state in which the snare loop of the diathermic snare according to the seventh embodiment is shifted to a rotation restriction position.

At the time the snare loop 45 is turned in the desired direction, the slider 48 is moved forward relative to the operation section body 47 as shown by an arrow A4 in FIG. 18. In this case, after the reception portion body 52a abuts on the stopper member 51 and stops, the slider 48 is further advanced. Thus, the spring member 52b is compressed and the reception portion body 52a is pressed on the stopper member 51. Thereby, the snare loop 45 turned in the desired direction is fixed (rotation restriction position). Therefore, the direction of the snare loop 45 will not change even if an external force acts on it.

Next, a description is given of the operation of the diathermic snare 41 in the case where the diathermic snare 41 is inserted in the body, for example, through the channel of the endoscope, and a polyp in a body cavity is resected by the diathermic snare 41 while conducting an endoscopic observation. To start with, the diathermic snare 41 in the state in which the snare loop 45 is retreated in the sheath 42 in advance, as shown in FIG. 15, is introduced into the body cavity through the channel of the endoscope. The diathermic snare 41 is guided to a polyp, which is a target part to be resected in the body cavity. At this time, it is desirable that the snare loop 45 be situated in parallel with the polyp.

If the snare loop 45 is not situated in the desired direction, the direction of the snare loop 45 is adjusted in the method illustrated in FIG. 17. In the adjustment work, the slider 48 of operation section 43 is slightly moved backward, as indicated by the arrow A3 in FIG. 17, from the rotation restriction position. Thereby, the reception portion body 52a moves away from the stopper member 51, and the rotation restriction position is changed to the restriction release position. In this state (restriction release position), the sheath 42 is held and the operation section 43 is rotated about its axis.

After the operation section 43 is rotated and the direction of the snare loop 45 is changed, the slider 48 is strongly pushed forward. Thereby, the snare loop 45 is fixed in the desired direction. In this state, a work for capturing the polyp is performed.

In the work of capturing the polyp, the polyp is placed within the snare loop 45 and captured, following which the slider 48 is pulled to tightly bind the polyp. In this state, electric power is supplied to the snare loop 45, thereby resecting the polyp. The resected polyp is held by grasping forceps (not shown) or the like and is recovered. In this case, the polyp is taken out of the body along with the grasping forceps (not shown) and is recovered. Thus, the treatment is completed.

The seventh embodiment with the above structure has the following advantages. In this embodiment, the slider 48 is strongly pushed forward, whereby the stopper reception portion 52 is pressed on the stopper member 51 against the urging force of the spring member 52*b* and the rotation of the operation section 43 is restricted. Therefore, after the snare loop 45 is adjusted in the desired direction in the restriction release position, the direction of the snare loop 45 can be fixed by the simple work of strongly pushing the slider 48 forward. As a result, during the polyp capturing operation, the snare loop 45 can be situated in parallel with the polyp and the polyp can easily be captured.

FIG. 19A through FIG. 21B show an eighth embodiment of the invention. In the eighth embodiment, the structure of the engaging mechanism 53 for restricting the rotation of the snare loop 45 of the diathermic snare 41 according to the seventh embodiment (see FIGS. 14 to 18) is altered as follows.

In the diathermic snare 41 of this embodiment, as shown in FIG. 19A, a plurality of slits 61 are formed at the proximal end portion of the stopper member 51. Each slit 61, as shown in FIG. 19B, extends radially from the axial center of the stopper member 51.

The stopper reception portion 52 of the seventh embodiment, which is provided at the distal end of the slider 48, is replaced with a stopper reception portion 62, as shown in FIG. 19C. The stopper reception portion 62 has a wing-like engaging portion 63. As is shown in FIG. 19C, the engaging portion 63 has a pair of projection portions 63*a* projecting from the outer peripheral surface of the stopper reception portion 62. Each projection portion 63*a* can be engaged with the slits 61 of the stopper member 51.

The operation of the diathermic snare 41 according to the eighth embodiment with the above structure is described. When the diathermic cutter 41 of this embodiment is used, the diathermic cutter 41, like the seventh embodiment, is set in one of the state in which the snare loop 45 is retreated in the sheath 42 as shown in FIG. 19A, and the state in which the slider 48 is moved forward and the snare loop 45 is projected as shown in FIG. 21A.

Figure 20:
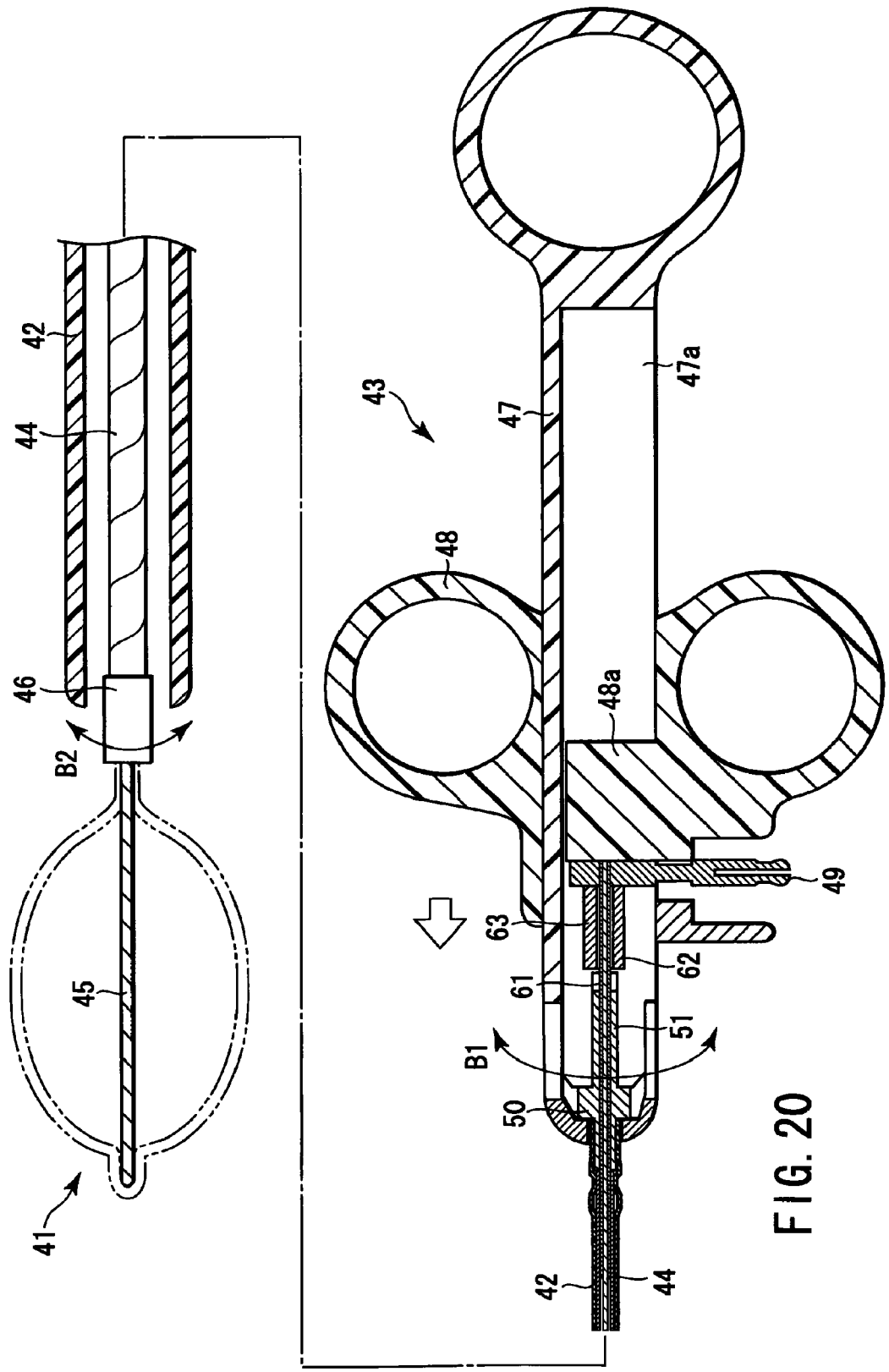
FIG. 20 is a vertical cross-sectional view of the main part, illustrating an operation of projecting the snare loop of the diathermic snare according to the eighth embodiment, and rotating the snare loop about its axis.

When the slider 48 is moved forward to project the snare loop 45, the engaging portion 63 of the stopper reception portion 62 abuts on a wall face between the slits 61 of stopper member 51 and stops, as shown in FIG. 20, before the engaging portion 63 is engaged with the slits 61 of stopper member 51.

In this state, the operation section 43 is rotated about its axis, as indicated by an arrow B1 in FIG. 20. Accordingly, the snare loop 45 is rotated about its axis, as indicated by an arrow B2 in FIG. 20, and the direction of the snare loop 45 is changed.

After the snare loop 45 is adjusted in the desired direction, the slider 48 is pushed forward, as shown in FIG. 21A, thereby to engage the engaging portion 63 of stopper reception portion 62 with the slits 61 of stopper member 51. In this case, as shown in FIG. 21B, the paired projection portions 63*a* of stopper reception portion 62 are engaged with the slits 61 of stopper member 51. Thus, the stopper reception portion 62 is prevented from rotating about its axis relative to the stopper member 51. As a result, the rotation of the snare loop 45 is prevented, and the snare loop 45 is kept in the desired direction. In the other respects, the eighth embodiment is the same as the seventh embodiment.

The eighth embodiment with the above structure has the following advantages. In this embodiment, the slider 48 is pushed forward after the snare loop 45 is adjusted in the desired direction. Thereby, the engaging portion 63 of stopper reception portion 62 is engaged with the slits 61 of stopper member 51. Thus, as shown in FIG. 21B, the engaging portion 63 of stopper reception portion 62 is prevented from rotating relative to the stopper member 51. Therefore, the direction of the snare loop 45 can be fixed, and during the polyp capturing operation the snare loop 45 can be situated in parallel with the polyp and the polyp can easily be captured. The present invention is not limited to the above-described embodiments. For example, in the first to eighth embodiments, treatment instruments for cutting and resection with use of high-frequency power are described. Alternatively, this invention is applicable to non-high-frequency treatment instruments such as cutting blades. The instruments usable in this invention are not limited to those for cutting and resection, and this invention is applicable to instruments configured to be used with their directions being optimally rotated and adjusted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic treatment instrument comprising:
a flexible sheath;
an operation member inserted in the sheath and advanced/retreated in an axial direction with respect to the sheath;
a treatment section provided at a distal end portion of the operation member and projected/retreated from/in the distal end portion of the sheath by the operation member;
a proximal-side operation section provided at a proximal end portion of the sheath, the operation section including a slider member which advances/retreats the operation member in the axial direction, and a rotation drive section which rotates the treatment section about an axis of the sheath via the operation member;
a stopper member provided at the sheath;
a stopper abutment portion provided to a backward side of the stopper member and advanced/retreated in the axial direction together with the operation member due to an operation of the slider member, the stopper abutment portion being advanced/retreated between a rotation restriction position where the stopper abutment portion is abutted upon the stopper member and a restriction release position where the stopper abutment portion is separated from the stopper member;
a position adjusting section which adjusts a position of the treatment section to a desired position in a circumferential direction of the sheath by rotating the operation member and the stopper abutment portion about the axis of the sheath due to an operation of the rotation drive section in a state that the stopper abutment portion is located to the restriction release position; and
a rotation restriction section which restricts a rotation of the stopper abutment portion about the axis of the sheath by pressing the stopper abutment portion on the stopper member in a state that the treatment portion is adjusted to the desired position by the position adjusting section and the stopper abutment portion is advanced from the restriction released position to the rotation restriction position due to the operation of the slider member, and thereby the treatment portion is fixed to the desired position;

wherein a stroke of motion of the slider member is configured to be longer than a distance of movement of the stopper abutment portion from the restriction release position to the rotation restriction position, when the stopper abutment portion is moved due to the operation of the slider member.

2. The endoscopic treatment instrument according to claim 1, wherein the stopper member serves also as a restriction member which restricts a length of projection of the treatment section.

3. The endoscopic treatment instrument according to claim 1, wherein the treatment section has a blade laterally extending relative to the axis of the sheath.

4. The endoscopic treatment instrument according to claim 1, wherein the stopper member is provided at a distal end portion of the sheath, and the abutment portion is provided at a proximal end portion of the treatment section.

5. The endoscopic treatment instrument according to claim 1, wherein the rotation restriction section includes an engaging mechanism which restricts the rotation of the stopper abutment portion about the axis of the sheath by a frictional force between the stopper member and the stopper abutment portion.

6. The endoscopic treatment instrument according to claim 1, wherein the stopper abutment portion located to the rotation restriction position is pressed on the stopper member by sliding forward the slide member.

7. The endoscopic treatment instrument according to claim 1, wherein:
- the stopper member includes an engage abutment portion,
- the stopper abutment portion includes an engage portion which detachably engages with respect to the engage abutment portion; and
- the rotation restriction section includes an engaging mechanism which restricts the rotation of the stopper abutment portion about the axis of the sheath by engaging the engage portion with respect to the engage abutment portion.

* * * * *